(12) United States Patent
Burgermeister et al.

(10) Patent No.: US 9,393,135 B2
(45) Date of Patent: Jul. 19, 2016

(54) BALLOON EXPANDABLE BIOABSORBABLE DRUG ELUTING STENT

(75) Inventors: Robert Burgermeister, Bridgewater, NJ (US); Ramesh Marrey, Basking Ridge, NJ (US); Vipul Bhupendra Dave, Hillsborough, NJ (US); David Overaker, Annandale, NJ (US); Joseph H. Contiliano, Stewartsville, NJ (US); Qiang Zhang, Annandale, NJ (US)

(73) Assignee: Cardinal Health Switzerland 515 GmbH (CH)

( * ) Notice: Subject to any disclaimer, the term of this patent is extended or adjusted under 35 U.S.C. 154(b) by 445 days.

(21) Appl. No.: 11/747,500

(22) Filed: May 11, 2007

(65) Prior Publication Data

US 2008/0132995 A1    Jun. 5, 2008

Related U.S. Application Data

(60) Provisional application No. 60/747,160, filed on May 12, 2006.

(51) Int. Cl.
*A61F 2/915* (2013.01)
*A61L 31/04* (2006.01)
(Continued)

(52) U.S. Cl.
CPC .................. *A61F 2/915* (2013.01); *A61L 31/04* (2013.01); *A61L 31/16* (2013.01); *A61L 31/18* (2013.01); *A61F 2/82* (2013.01); *A61F 2002/825* (2013.01); *A61F 2002/91533* (2013.01); *A61F 2002/91558* (2013.01); *A61F 2002/91575* (2013.01); *A61F 2210/0004* (2013.01); *A61F 2220/0008* (2013.01); *A61F 2220/0075* (2013.01);
(Continued)

(58) Field of Classification Search
USPC ......................................................... 623/1.15
See application file for complete search history.

(56) References Cited

U.S. PATENT DOCUMENTS

| 6,042,606 A * | 3/2000 | Frantzen | 623/1.18 |
| 6,203,569 B1 * | 3/2001 | Wijay | 623/1.15 |

(Continued)

FOREIGN PATENT DOCUMENTS

| EP | 1698303 A1 | 3/2006 |
| WO | WO 00/71054 A1 | 11/2000 |

(Continued)

*Primary Examiner* — Yashita Sharma
*Assistant Examiner* — Rebecca Preston
(74) *Attorney, Agent, or Firm* — Dergosits & Noah LLP; Todd A. Noah

(57) ABSTRACT

A biocompatible material may be configured into any number of implantable medical devices including intraluminal stents. Polymeric materials may be utilized to fabricate any of these devices, including stents. The stents may be balloon expandable or self-expanding. The polymeric materials may include additives such as drugs or other bioactive agents as well as radiopaque agents. By preferential mechanical deformation of the polymer, the polymer chains may be oriented to achieve certain desirable performance characteristics. The stent has a plurality of hoop components interconnected by a plurality of flexible connectors. The hoop components are formed as a continuous series of substantially longitudinally or axially oriented radial strut members and alternating substantially circumferentially oriented radial arc members. The geometry of the struts and arcs is such that when the stent is expanded, it has very high strains within a relatively small region. This strain localization results in what is often referred to as "hinging", where the hinge is the small region within which the strains are very high.

39 Claims, 11 Drawing Sheets

(51) Int. Cl.
  *A61L 31/16* (2006.01)
  *A61L 31/18* (2006.01)
  *A61F 2/82* (2013.01)

(52) U.S. Cl.
  CPC . *A61F2230/0013* (2013.01); *A61F 2250/0018* (2013.01); *A61F 2250/0028* (2013.01); *A61F 2250/0029* (2013.01); *A61F 2250/0036* (2013.01); *A61F 2250/0062* (2013.01); *A61F 2250/0067* (2013.01); *A61F 2250/0098* (2013.01); *A61L 2300/416* (2013.01)

(56) References Cited

U.S. PATENT DOCUMENTS

| | | | |
|---|---|---|---|
| 6,241,762 B1* | 6/2001 | Shanley | 623/1.17 |
| 6,312,459 B1* | 11/2001 | Huang et al. | 623/1.15 |
| 6,312,460 B2* | 11/2001 | Drasler et al. | 623/1.15 |
| 6,540,774 B1* | 4/2003 | Cox | 623/1.15 |
| 6,605,110 B2* | 8/2003 | Harrison | 623/1.15 |
| 6,761,731 B2* | 7/2004 | Majercak | 623/1.11 |
| 2002/0045668 A1* | 4/2002 | Dang et al. | 514/649 |
| 2002/0055721 A1* | 5/2002 | Palasis et al. | 604/265 |
| 2003/0039696 A1* | 2/2003 | Porter | 424/486 |
| 2003/0105511 A1* | 6/2003 | Welsh et al. | 623/1.15 |
| 2003/0224033 A1* | 12/2003 | Li et al. | 424/423 |
| 2004/0106985 A1 | 6/2004 | Jang | |
| 2004/0106987 A1 | 6/2004 | Palasis et al. | |
| 2004/0138737 A1* | 7/2004 | Davidson et al. | 623/1.35 |
| 2004/0148014 A1 | 7/2004 | Nuutinen et al. | |
| 2004/0249442 A1* | 12/2004 | Fleming et al. | 623/1.15 |
| 2004/0253203 A1* | 12/2004 | Hossainy et al. | 424/78.08 |
| 2005/0021131 A1* | 1/2005 | Venkatraman et al. | 623/1.19 |
| 2005/0098914 A1* | 5/2005 | Varma et al. | 264/108 |
| 2005/0182479 A1* | 8/2005 | Bonsignore et al. | 623/1.15 |
| 2005/0187615 A1 | 8/2005 | Williams et al. | |
| 2005/0261757 A1* | 11/2005 | Shanley | A61F 2/915 623/1.15 |
| 2006/0020330 A1* | 1/2006 | Huang et al. | 623/1.49 |
| 2006/0076708 A1 | 4/2006 | Huang et al. | |
| 2006/0085059 A1* | 4/2006 | Ehrlinspiel et al. | 623/1.15 |
| 2006/0259126 A1* | 11/2006 | Lenz | 623/1.16 |
| 2007/0073384 A1* | 3/2007 | Brown | A61F 2/91 623/1.16 |
| 2007/0283552 A1 | 12/2007 | Gale et al. | |
| 2007/0290412 A1 | 12/2007 | Capek et al. | |
| 2007/0293938 A1 | 12/2007 | Gale et al. | |
| 2009/0096137 A1 | 4/2009 | Williams et al. | |

FOREIGN PATENT DOCUMENTS

WO WO 2004/045653 A2 6/2004
WO WO 2006/005026 A2 1/2006

* cited by examiner

BALLOON EXPANDABLE BIOABSORBABLE DRUG ELUTING STENT

CROSS-REFERENCE TO RELATED APPLICATIONS

This application claims the benefit of U.S. Provisional Application Ser. No. 60/747,160 filed May 12, 2006.

BACKGROUND OF THE INVENTION

1. Field of the Invention

The present invention relates to intraluminal polymeric stents, and more particularly to intraluminal polymeric stents formed from blends of polymers, blends of polymers and plasticizers, blends of polymers and radiopaque agents, blends of polymers, plasticizers and radiopaque agents, blends of polymers, radiopaque agents and therapeutic agents, blends of polymers, plasticizers, radiopaque agents and therapeutic agents, or any combination thereof. These polymeric stents may have a modified molecular orientation due to the application of stress.

2. Discussion of the Related Art

Currently manufactured intraluminal stents do not adequately provide sufficient tailoring of the properties of the material forming the stent to the desired mechanical behavior of the device under clinically relevant in-vivo loading conditions. Any intraluminal device should preferably exhibit certain characteristics, including maintaining vessel patency through an acute and/or chronic outward force that will help to remodel the vessel to its intended luminal diameter, preventing excessive radial recoil upon deployment, exhibiting sufficient fatigue resistance and exhibiting sufficient ductility so as to provide adequate coverage over the full range of intended expansion diameters.

Accordingly, there is a need to develop materials and the associated processes for manufacturing intraluminal stents that provide device designers with the opportunity to engineer the device to specific applications.

SUMMARY OF THE INVENTION

The present invention overcomes the limitations of applying conventionally available materials to specific intraluminal therapeutic applications as briefly described above.

In accordance with one aspect of the present invention, a stent comprises a plurality of hoop components interconnected by a plurality of flexible connectors. The hoop components are formed as a continuous series of substantially longitudinally (axially) oriented radial strut members and alternating substantially circumferentially oriented radial arc members. The geometry of the struts and arcs is such that when the stent is expanded, it has very high strains within a relatively small region. This strain localization results in what is often referred to as "hinging", where the hinge is the small region within which the strains are very high.

In accordance with another aspect, the present invention is directed to an implantable medical device. The medical device comprising a frame structure, the frame structure including at least one element having one or more sections being formed from at least one polymer and at least one plasticizer blended to create a deformable frame structure having increased toughness, and wherein at least one of the one or more sections having an amount of alignment of the polymer chains of the blend in a direction of the at least one or more sections greater than an amount of alignment of the polymer chains of the blend in a direction of another of the at least one or more sections.

In accordance with another aspect, the present invention is directed to an implantable medical device. The medical device comprising a frame structure, the frame structure including at least one element having one or more sections being formed from at least one polymer and at least one plasticizer blended to create a deformable frame structure having increased toughness, and wherein each of the one or more sections having a substantially equal amount of alignment of the polymer chains of the blend in directions substantially parallel to the directions of each of the at least one or more sections respectively.

In accordance with another aspect, the present invention is directed to an implantable medical device. The medical device comprising a frame structure, the frame structure including at least one element having one or more sections being formed from at least one polymer, at least one plasticizer and at least one therapeutic agent blended to create a deformable frame structure having increased toughness, and wherein at least one of the one or more sections having an amount of alignment of the polymer chains of the blend in a direction of the at least one or more sections greater than an amount of alignment of the polymer chains of the blend in a direction of another of the at least one or more sections.

In accordance with another aspect, the present invention is directed to an implantable medical device. The medical device comprising a frame structure, the frame structure including at least one element having one or more sections being formed from at least one polymer, at least one plasticizer and at least one therapeutic agent blended to create a deformable frame structure having increased toughness, and wherein each of the one or more sections having a substantially equal amount of alignment of the polymer chains of the blend in directions substantially parallel to the directions of each of the at least one or more sections respectively.

In accordance with another aspect, the present invention is directed to an implantable medical device. The medical device comprising a frame structure, the frame structure including at least one element having one or more sections being formed from at least one polymer and at least one plasticizer blended to create a deformable frame structure having increased toughness, and wherein at least one of the one or more sections having an amount of alignment of the polymer chains of the blend in a direction of the at least one or more sections greater than an amount of alignment of the polymer chains of the blend in a direction of another of the at least one or more sections, and at least one therapeutic agent affixed to the frame structure.

In accordance with another aspect, the present invention is directed to an implantable medical device. The medical device comprising a frame structure, the frame structure including at least one element having one or more sections being formed from at least one polymer and at least one plasticizer blended to create a deformable frame structure having increased toughness, and wherein each of the one or more sections having a substantially equal amount of alignment of the polymer chains of the blend in directions substantially parallel to the directions of each of the at least one or more sections respectively, and at least one therapeutic agent affixed to the frame structure.

In accordance with another aspect, the present invention is directed to an implantable medical device. The medical device comprising a frame structure, the frame structure including at least one element having one or more sections being formed from at least one polymer, at least one plasticizer and a radiopaque material blended to create a deformable frame structure having increased toughness, and wherein at least one of the one or more sections having an amount of alignment of the polymer chains of the blend in a direction of the at least one or more sections greater than an amount of alignment of the polymer chains of the blend in a direction of another of the at least one or more sections.

In accordance with another aspect, the present invention is directed to an implantable medical device. The medical device comprising a frame structure, the frame structure including at least one element having one or more sections being formed from at least one polymer, at least one plasticizer and a radiopaque material blended to create a deformable frame structure having increased toughness, and wherein each of the one or more sections having a substantially equal amount of alignment of the polymer chains of the blend in directions substantially parallel to the directions of each of the at least one or more sections respectively.

In accordance with another aspect, the present invention is directed to an implantable medical device. The medical device comprising a frame structure, the frame structure including at least one element having one or more sections being formed from at least one polymer, at least one plasticizer, a radiopaque material and at least one therapeutic agent blended to create a deformable frame structure having increased toughness, and wherein at least one of the one or more sections having an amount of alignment of the polymer chains of the blend in a direction of the at least one or more sections greater than an amount of alignment of the polymer chains of the blend in a direction of another of the at least one or more sections.

In accordance with another aspect, the present invention is directed to an implantable medical device. The medical device comprising a frame structure, the frame structure including at least one element having one or more sections being formed from at least one polymer, at least one plasticizer, a radiopaque material and at least one therapeutic agent blended to create a deformable frame structure having increased toughness, and wherein each of the one or more sections having a substantially equal amount of alignment of the polymer chains of the blend in directions substantially parallel to the directions of each of the at least one or more sections respectively.

In accordance with another aspect, the present invention is directed to an implantable medical device. The medical device comprising a frame structure, the frame structure including at least one element having one or more sections being formed from at least one polymer, at least one plasticizer and a radiopaque material blended to create a deformable frame structure having increased toughness, and wherein at least one of the one or more sections having an amount of alignment of the polymer chains of the blend in a direction of the at least one or more sections greater than an amount of alignment of the polymer chains of the blend in a direction of another of the at least one or more sections, and at least one therapeutic agent affixed to the frame structure.

In accordance with another aspect, the present invention is directed to an implantable medical device. The medical device comprising a frame structure, the frame structure including at least one element having one or more sections being formed from at least one polymer, at least one plasticizer and a radiopaque material blended to create a deformable frame structure having increased toughness, and wherein each of the one or more sections having a substantially equal amount of alignment of the polymer chains of the blend in directions substantially parallel to the directions of each of the at least one or more sections respectively, and at least one therapeutic agent affixed to the frame structure.

The biocompatible materials for implantable medical devices of the present invention may be utilized for any number of medical applications, including vessel patency devices, such as vascular stents, biliary stents, ureter stents, vessel occlusion devices such as atrial septal and ventricular septal occluders, patent foramen ovale occluders and orthopedic devices such as fixation devices.

The biocompatible materials of the present invention comprise unique compositions and designed-in properties that enable the fabrication of stents and/or other implantable medical device that are able to withstand a broader range of loading conditions than currently available stents and/or other implantable medical devices. More particularly, the molecular structure designed into the biocompatible materials facilitates the design of stents and/or other implantable medical devices with a wide range of geometries that are adaptable to various loading conditions.

The intraluminal devices of the present invention may be formed out of any number of biocompatible polymeric materials. In order to achieve the desired mechanical properties, the polymeric material, whether in the raw state or in the tubular or sheet state may be physically deformed to achieve a certain degree of alignment of the polymer chains. This alignment may be utilized to enhance the physical and/or mechanical properties of one or more components of the stent.

The intraluminal devices of the present invention may also be formed from blends of polymeric materials, blends of polymeric materials and plasticizers, blends of polymeric materials and therapeutic agents, blends of polymeric materials and radiopaque agents, blends of polymeric materials with both therapeutic and radiopaque agents, blends of polymeric materials with plasticizers and therapeutic agents, blends of polymeric materials with plasticizers and radiopaque agents, blends of polymeric materials with plasticizers, therapeutic agents and radiopaque agents, and/or any combination thereof. By blending materials with different properties, a resultant material may have the beneficial characteristics of each independent material. For example, stiff and brittle materials may be blended with soft and elastomeric materials to create a stiff and tough material. In addition, by blending either or both therapeutic agents and radiopaque agents together with the other materials, higher concentrations of these materials may be achieved as well as a more homogeneous dispersion. Various methods for producing these blends include solvent and melt processing techniques.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Implantable medical devices may be fabricated from any number of suitable biocompatible materials, including polymeric materials. The internal structure of these polymeric materials may be altered utilizing mechanical and/or chemical manipulation of the polymers. These internal structure modifications may be utilized to create devices having specific gross characteristics such as crystalline and amorphous morphology and orientation as is explained in detail subsequently. Although the present invention applies to any number of implantable medical devices, for ease of explanation, the following detailed description will focus on an exemplary stent.

In accordance with the present invention, implantable medical devices may be fabricated from any number of biocompatible materials, including polymeric materials. These polymeric materials may be non-degradable, biodegradable and/or bioabsorbable. These polymeric materials may be formed from single polymers, blends of polymers and blends of polymers and plasticizers. In addition, other agents such as drugs and/or radiopaque agents may be blended with the materials described above or affixed or otherwise added thereto. A number of chemical and/or physical processes may be utilized to alter the chemical and physical properties of the materials and ultimately the final devices.

Exemplary Devices

Figure 1:
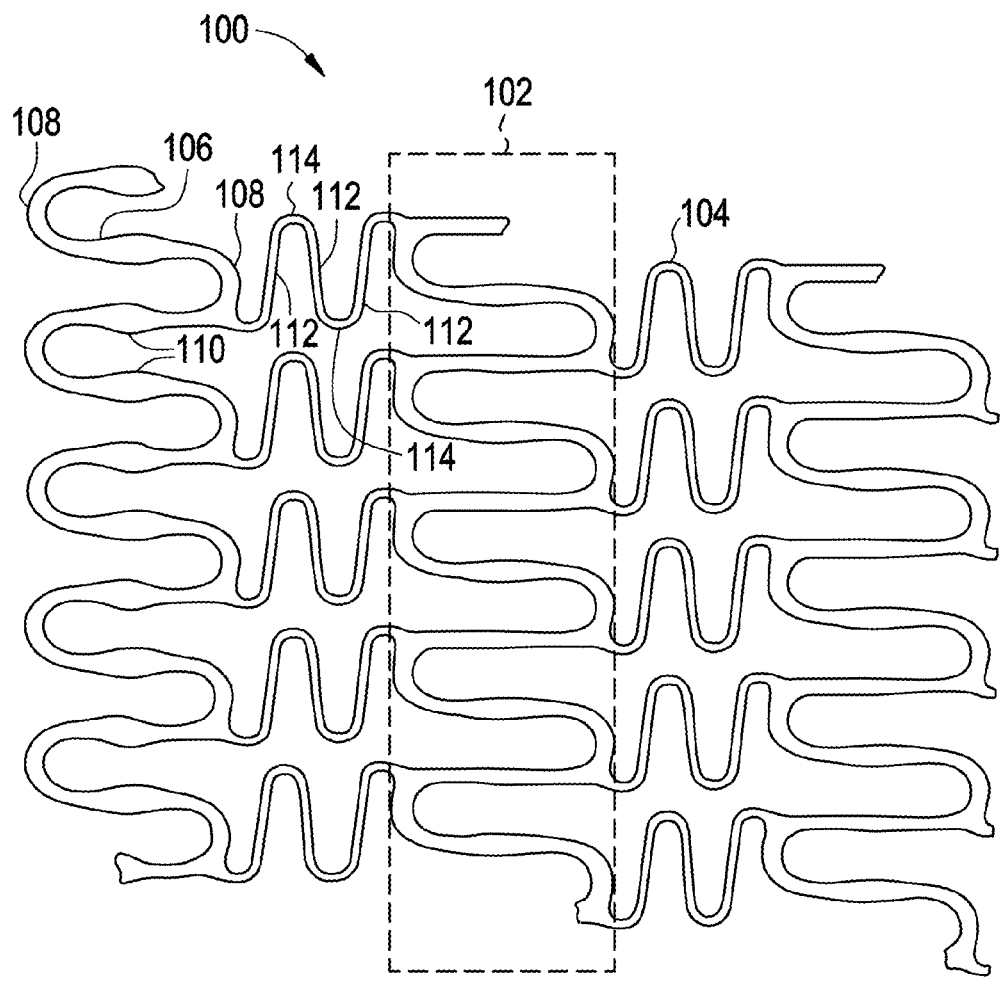
FIG. 1 is a planar representation of an exemplary stent fabricated from biocompatible materials in accordance with the present invention.

Referring to FIG. 1, there is illustrated a partial planar view of an exemplary stent 100 in accordance with the present invention. The exemplary stent 100 comprises a plurality of hoop components 102 interconnected by a plurality of flexible connectors 104. The hoop components 102 are formed as a continuous series of substantially longitudinally (axially) oriented radial strut members 106 and alternating substantially circumferentially oriented radial arc members 108. Although shown in planar view, the hoop components 102 are essentially ring members that are linked together by the flexible connectors 104 to form a substantially tubular stent structure. The combination of radial strut members 106 and alternating radial arc members 108 form a substantially sinusoidal pattern. Although the hoop components 102 may be designed with any number of design features and assume any number of configurations, in the exemplary embodiment, the radial strut members 106 are wider in their central regions 110. This design feature may be utilized for a number of purposes, including, increased surface area for drug delivery.

The flexible connectors 104 are formed from a continuous series of flexible strut members 112 and alternating flexible arc members 114. The flexible connectors 104, as described above, connect adjacent hoop components 102 together. In this exemplary embodiment, the flexible connectors 104 have a substantially N-shape with one end being connected to a radial arc member on one hoop component and the other end being connected to a radial arc member on an adjacent hoop component. As with the hoop components 102, the flexible connectors 104 may comprise any number of design features and any number of configurations. In the exemplary embodiment, the ends of the flexible connectors 104 are connected to different portions of the radial arc members of adjacent hoop components for ease of nesting during crimping of the stent. It is interesting to note that with this exemplary configuration, the radial arcs on adjacent hoop components are slightly out of phase, while the radial arcs on every other hoop component are substantially in phase. In addition, it is important to note that not every radial arc on each hoop component need be connected to every radial arc on the adjacent hoop component.

It is important to note that any number of designs may be utilized for the flexible connectors or connectors in an intraluminal scaffold or stent. For example, in the design described above, the connector comprises two elements, substantially longitudinally oriented strut members and flexible arc members. In alternate designs, however, the connectors may comprise only a substantially longitudinally oriented strut member and no flexible arc member or a flexible arc connector and no substantially longitudinally oriented strut member.

The substantially tubular structure of the stent 100 provides either temporary or permanent scaffolding for maintaining patency of substantially tubular organs, such as arteries. The stent 100 comprises a luminal surface and an abluminal surface. The distance between the two surfaces defines the wall thickness. The stent 100 has an unexpanded diameter for delivery and an expanded diameter, which roughly corresponds to the normal diameter of the organ into which it is delivered. As tubular organs such as arteries may vary in diameter, different size stents having different sets of unexpanded and expanded diameters may be designed without departing from the spirit of the present invention. As described herein, the stent 100 may be formed from any number of polymeric materials. These stents may be prepared from other materials such as polymer-metal composites. Exemplary materials include the utilization of biostable metal-biostable polymers, biostable metal-bioabsorbable polymers, bioabsorbable metal-biostable polymers, and bioabsorbable metal-bioabsorbable polymers. These materials may be used for the full stent or portions thereof.

Preferred Embodiments

Figure 10:
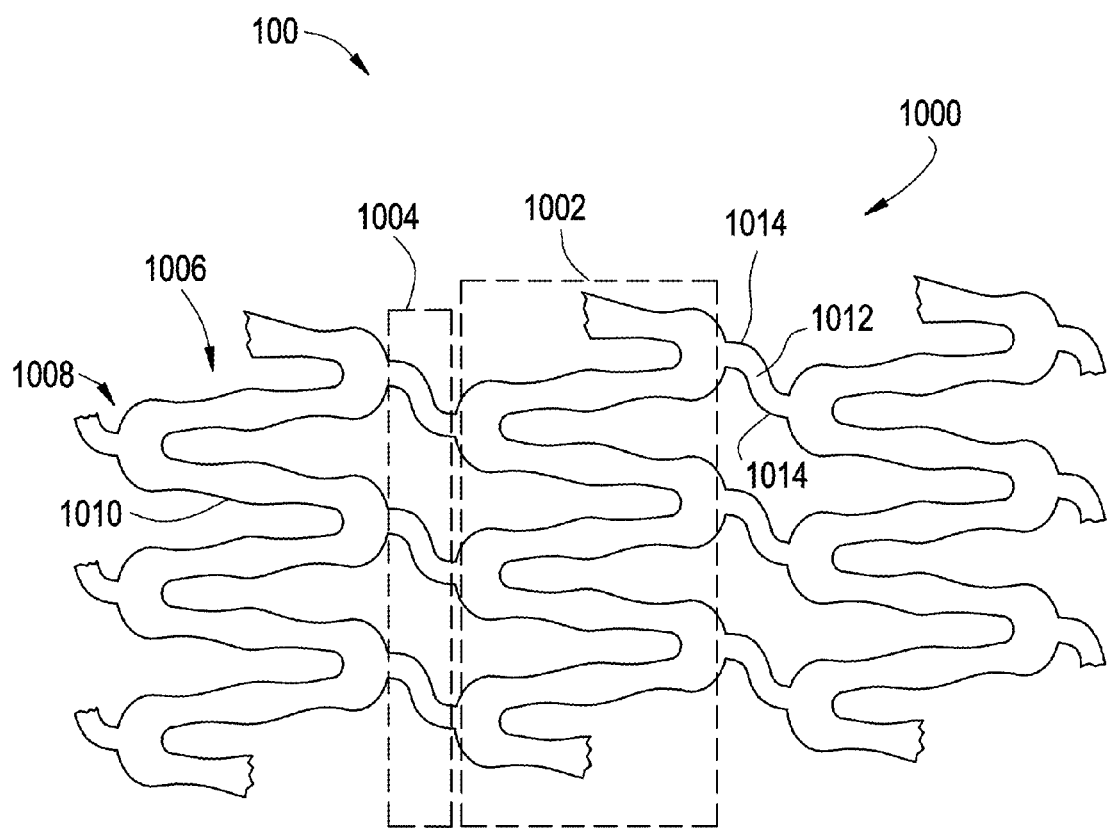
FIG. 10 is a planar representation of a stent fabricated from biocompatible materials in accordance with the present invention.
Figure 11:
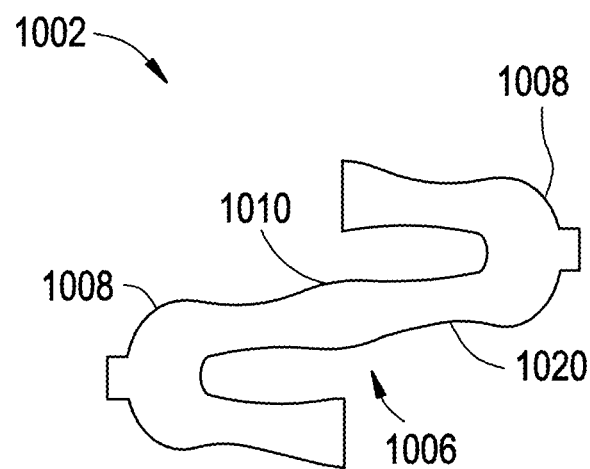
FIG. 11 is a representation of a hoop component illustrating the hinging region of an undeformed stent according to one embodiment of the present invention.
Figure 12:
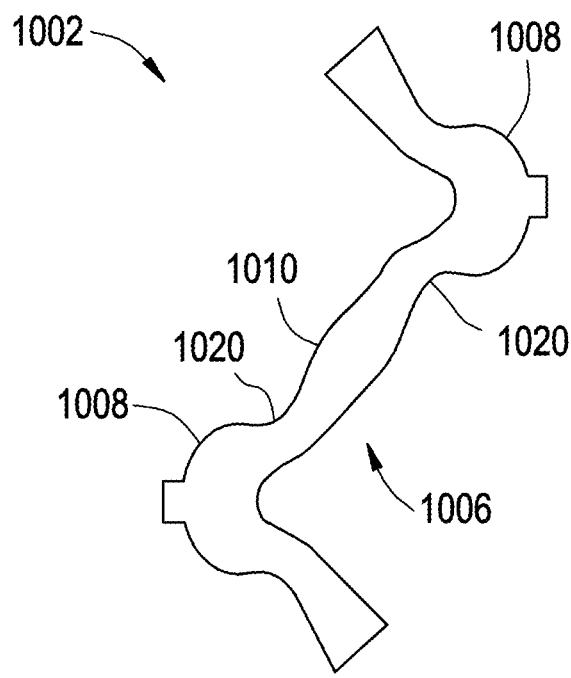
FIG. 12 is a representation of a hoop component illustrating the hinging region of an expanded stent according to one embodiment of the present invention.

Referring to FIG. 10, there is illustrated a partial planar view of a stent 100 in accordance with the present invention. The preferred stent 1000 comprises a plurality of hoop components 1002 interconnected by a plurality of flexible connectors 1004. The hoop components 1002 are formed as a continuous series of substantially longitudinally (axially) oriented radial strut members 1006 and alternating substantially circumferentially oriented radial arc members 1008. As illustrated in FIGS. 10 through 12, the radial arc member 1008 has an outside radius and an inside radius with a width there between. Although shown in planar view, the hoop components 1002 are essentially ring members that are linked together by the flexible connectors 1004 to form a substantially tubular stent structure. The combination of radial strut members 1006 and alternating radial arc members 1008 form a substantially sinusoidal pattern. Although the hoop components 1002 may be designed with any number of design features and assume any number of configurations, in the preferred embodiment, the radial strut members 1006 are wider in their central regions 1010. This design feature may be utilized for a number of purposes, including, increased surface area for drug delivery.

The geometry of the struts 1006 and arcs 1008 is such that when the stent 1000 is expanded, it has very high strains within a relatively small predetermined region. This strain localization results in what is often referred to as "hinging", where the hinge is the small region within which the strains are very high. FIG. 11 is a representation of a hoop component 1002 illustrating the predetermined hinging region 1020 according to one embodiment of the present invention in the undeformed ("as-cut") configuration. FIG. 12 is a representation of a hoop component 1002 illustrating the hinging region 1020 according to one embodiment of the present invention in the deformed ("expanded") configuration. In a preferred embodiment of the invention, the concentrated strains in the predetermined region exceed the yield point, but are below the ultimate strain levels, of the polymeric frame. In one embodiment, the concentrated strain in the predetermined region is between 5 percent (0.05 in/in) and 150 percent (1.5 in/in), and preferably between 30 percent (0.30 in/in) and 80 percent (0.80 in/in).

Typically one would try to avoid hinging in a metal stent. Hinging, however, would be advantageous for a polymer stent because the polymer within the hinging region can become highly drawn and, thereby, oriented. Strain induced crystallization could also occur depending on the polymer used. The crystallization may vary the absorption time of the hinged region, such that the stent design can be utilized to vary the absorption time rather than material changes. In addition, highly drawn polymer will strain harden such that it will be stiffer and stronger upon unloading, which would be beneficial for controlling recoil and maximizing radial strength. A hinging design would also have a radial strength advantage since the structure would be geometrically stiffer due to the fact that the struts are more circumferentially aligned and the arcs are very wide. A hinging design with a focal deformation zone will also have less elastic strain energy and therefore would exhibit less recoil than a design with a larger deformed zone with high elastic strain energy.

The hinging is accomplished by creating a region 1020 at each end of each strut 1006 that has a small cross-sectional area relative to the adjacent geometry. The embodiment shown in FIGS. 11 and 12 has relatively wide radial arcs 1008 and "bulges" 1010 at the center of the radial struts 1006. The bulge 1010 is a region in the central portion of the radial strut 1006 that is wider than either end of the strut. Both the wider radial arcs 1008 and the bulges 1010 in the radial struts 1006 are stiffer in bending and therefore resist deformation during expansion, so that the hinge areas 1020 at the strut ends are forced to carry the majority of the deformation. This is depicted in the expanded configuration illustrated in FIG. 12. Since the radial arc 1008 is much stiffer, the strut 1006 ends have hinged (region 1020) in order to accommodate the expansion. The majority of the deformation (material strain) is therefore localized in the hinge regions 1020.

As illustrated in FIG. 10, the flexible connectors 1004 are formed from a flexible strut member 1012 with adjacent flexible arc members 1014. The flexible connectors 1004, as described above, connect adjacent hoop components 1002 together. In this preferred embodiment, the flexible connectors 1004 have a substantially S-shape with one end being connected to a radial arc member 1014 on one hoop component 1002 and the other end being connected to a radial arc member 1014 on an adjacent hoop component 1002. As with the hoop components 1002, the flexible connectors 1004 may comprise any number of design features and any number of configurations. In the illustrated embodiment, the ends of the flexible connectors 1004 are connected at the apices of radial arc members 1008 of adjacent hoop components 1002.

Alternatively, the ends of the flexible connectors 1004 may be connected at different locations, for example, at different points along the radial arcs 1008 similar to that shown in FIG. 1. The location of the connector 1004 ends (where the connector meets the arc) could be located anywhere along the path of the radial arc 1008 or even in the bulge 1010. The only limitation on the location of the flex connector 1004 end is that it does not intersect or interfere with the hinge region.

The S-shaped flex connector 1004 accommodates a phase shift between adjacent hoop components 1002, which provides bending flexibility to the stent 1000 structure. In addition, it is important to note that not every radial arc on each hoop component need be connected to every radial arc on the adjacent hoop component.

The embodiment disclosed here shows an S-shaped flex connector 1004. Any of a number of connector geometries could be used in place of the "S" connector 1004 in order to connect adjacent hoop sections 1002 together. A larger phase shift between adjacent hoop sections 1002 or even alternating phase shift from one hoop section 1002 to the next could also be considered. The embodiment shown has a continuous phase shift along the length.

It is important to note that any number of designs may be utilized for the flexible connectors or connectors in an intraluminal scaffold or stent. For example, in the design described above, the connector comprises two elements, substantially longitudinally oriented strut members and flexible arc members. In alternate designs, however, the connectors may comprise only a substantially longitudinally oriented strut member and no flexible arc member or a flexible arc connector and no substantially longitudinally oriented strut member.

The substantially tubular structure of the stent 1000 provides either temporary or permanent scaffolding for maintaining patency of substantially tubular organs, such as arteries. The stent 1000 comprises a luminal surface and an abluminal surface. The distance between the two surfaces defines the wall thickness. The stent 1000 has an unexpanded diameter for delivery and an expanded diameter, which roughly corresponds to the normal diameter of the organ into which it is delivered. As tubular organs such as arteries may vary in diameter, different size stents having different sets of unexpanded and expanded diameters may be designed without departing from the spirit of the present invention. As described herein, the stent 1000 may be formed from any number of polymeric materials. These stents may be prepared from other materials such as polymer-metal composites. Exemplary materials include the utilization of biostable metal-biostable polymers, biostable metal-bioabsorbable polymers, bioabsorbable metal-biostable polymers, and bioabsorbable metal-bioabsorbable polymers. These materials may be used for the full stent or portions thereof.

Material Characteristics

Accordingly, in one exemplary embodiment, an intraluminal scaffold element may be fabricated from a non-metallic material such as a polymeric material including non-crosslinked thermoplastics, cross-linked thermosets, composites and blends thereof. There are typically three different forms in which a polymer may display the mechanical properties associated with solids; namely, as a crystalline structure, as a semi-crystalline structure and/or as an amorphous structure. All polymers are not able to fully crystallize, as a high degree of molecular regularity within the polymer chains is essential for crystallization to occur. Even in polymers that do crystallize, the degree of crystallinity is generally less than one hundred percent. Within the continuum between fully crystalline and amorphous structures, there are two thermal transitions possible; namely, the crystal-liquid transition (i.e. melting point temperature, $T_m$) and the glass-liquid transition (i.e. glass transition temperature, $T_g$). In the temperature range between these two transitions there may be a mixture of orderly arranged crystals and chaotic amorphous polymer domains.

The Hoffman-Lauritzen theory of the formation of polymer crystals with "folded" chains owes its origin to the discovery in 1957 that thin single crystals of polyethylene may be grown from dilute solutions. Folded chains are preferably required to form a substantially crystalline structure. Hoffman and Lauritzen established the foundation of the kinetic theory of polymer crystallization from "solution" and "melt" with particular attention to the thermodynamics associated with the formation of chain-folded nuclei.

Crystallization from dilute solutions is required to produce single crystals with macroscopic perfection (typically magnifications in the range of about 200× to about 400×). Polymers are not substantially different from low molecular weight compounds such as inorganic salts in this regard. Crystallization conditions such as temperature, solvent and solute concentration may influence crystal formation and final form. Polymers crystallize in the form of thin plates or "lamellae." The thickness of these lamellae is on the order of ten nanometers (10 nm). The dimensions of the crystal plates perpendicular to the small dimensions depend on the conditions of the crystallization but are many times larger than the thickness of the platelets for a well-developed crystal. The chain direction within the crystal is along the short dimension of the crystal, which indicates that, the molecule folds back and forth (e.g. like a folded fire hose) with successive layers of folded molecules resulting in the lateral growth of the platelets. A crystal does not consist of a single molecule nor does a molecule reside exclusively in a single crystal. The loop formed by the chain as it emerges from the crystal turns around and reenters the crystal. The portion linking the two crystalline sections may be considered amorphous polymer. In addition, polymer chain ends disrupt the orderly fold patterns of the crystal, as described above, and tend to be excluded from the crystal. Accordingly, the polymer chain ends become the amorphous portion of the polymer. Therefore, no currently known polymeric material may be one-hundred percent crystalline. Post polymerization processing conditions dictate the crystal structure to a substantial extent.

Single crystals are not observed in crystallization from bulk processing. Bulk crystallized polymers from melt exhibits domains called "spherulites" that are symmetrical around a center of nucleation. The symmetry is perfectly circular if the development of the spherulite is not impinged by contact with another expanding spherulite. Chain folding is an essential feature of the crystallization of polymers from the molten state. Spherulites are comprised of aggregates of "lamellar" crystals radiating from a nucleating site. Accordingly, there is a relationship between solution and bulk grown crystals.

The spherical symmetry develops with time. Fibrous or lathlike crystals begin branching and fanning out as in dendritic growth. As the lamellae spread out dimensionally from the nucleus, branching of the crystallites continue to generate the spherical morphology. Growth is accomplished by the addition of successive layers of chains to the ends of the radiating laths. The chain structure of polymer molecules suggests that a given molecule may become involved in more than one lamella and thus link radiating crystallites from the same or adjacent spherulites. These interlamellar links are not possible in spherulites of low molecular weight compounds, which show poorer mechanical strength as a consequence.

The molecular chain folding is the origin of the "Maltese" cross, which identifies the spherulite under crossed polarizers. For a given polymer system, the crystal size distribution is influenced by the initial nucleation density, the nucleation rate, the rate of crystal growth, and the state of orientation. When the polymer is subjected to conditions in which nucleation predominates over radial growth, smaller crystals result. Larger crystals will form when there are relatively fewer nucleation sites and faster growth rates. The diameters of the spherulites may range from about a few microns to about a few hundred microns depending on the polymer system and the crystallization conditions.

Therefore, spherulite morphology in a bulk-crystallized polymer involves ordering at different levels of organization; namely, individual molecules folded into crystallites that in turn are oriented into spherical aggregates. Spherulites have been observed in organic and inorganic systems of synthetic, biological, and geological origin including moon rocks and are therefore not unique to polymers.

Stress induced crystallinity is important in film and fiber technology. When dilute solutions of polymers are stirred rapidly, unusual structures develop which are described as having a "shish kebab" morphology. These consist of chunks of folded chain crystals strung out along a fibrous central column. In both the "shish" and the "kebab" portions of the structure, the polymer chains are parallel to the overall axis of the structure.

When a polymer melt is sheared and quenched to a thermally stable condition, the polymer chains are perturbed from their random coils to easily elongate parallel to the shear direction. This may lead to the formation of small crystal aggregates from deformed spherulites. Other morphological changes may occur, including spherulite to fibril transformation, polymorphic crystal formation change, reorientation of already formed crystalline lamellae, formation of oriented crystallites, orientation of amorphous polymer chains and/or combinations thereof.

Molecular orientation is important as it primarily influences bulk polymer properties and therefore will have a strong effect on the final properties that are essential for different material applications. Physical and mechanical properties such as permeability, wear, refractive index, absorption, degradation rates, tensile strength, yield stress, tear strength, modulus and elongation at break are some of the properties that will be influenced by orientation. Orientation is not always favorable as it promotes anisotropic behavior. Orientation may occur in several directions such as uniaxial, biaxial and multiaxial. It may be induced by drawing, rolling, calendaring, spinning, blowing, and any other suitable process, and is present in systems including fibers, films, tubes, bottles, molded and extruded articles, coatings, and composites. When a polymeric material is processed, there will be preferential orientation in a specific direction. Usually it is in the direction in which the process is conducted and is called the machine direction (MD). Many of the products are purposely oriented to provide improved properties in a particular direction. If a product is melt processed, it will have some degree of preferential orientation. In case of solvent processed materials, orientation may be induced during processing by methods such as shearing the polymer solution followed by immediate precipitation or quenching to the desired geometry in order to lock in the orientation during the shearing process. Alternately, if the polymers have rigid rod like chemical structure then it will orient during processing due to the liquid crystalline morphology in the polymer solution.

The orientation state will depend on the type of deformation and the type of polymer. Even though a material is highly deformed or drawn, it is not necessary to impart high levels of orientation as the polymer chains may relax back to their original state. This generally occurs in polymers that are very flexible at the draw temperature. Therefore, several factors may influence the state of orientation in a given polymer system, including rate of deformation for example, strain rate, shear rate, frequency, and the like, amount of deformation or draw ratio, temperature, molecular weight and its distribution, chain configuration for example, stereoregularity, geometrical isomers, and the like, chain architecture, for example, linear, branched, cross-linked, dendritic and the like, chain stiffness, for example, flexible, rigid, semi-rigid, and the like, polymer blends, copolymer types, for example, random, block, alternating, and the like, and the presence of additives, for example, plasticizers, hard and soft fillers, long and short fibers, therapeutic agents and the like.

Since polymers consist of two phases; namely, crystalline and amorphous, the effect of orientation will differ for these phases, and therefore the final orientation may not be the same for these two phases in a semi-crystalline polymer system. This is because the flexible amorphous chains will respond differently to the deformation and the loading conditions than the hard crystalline phase.

Different phases may be formed after inducing orientation and its behavior depends on the chemistry of the polymer backbone. A homogenous state such as a completely amorphous material would have a single orientation behavior. However, in polymers that are semi-crystalline, block copolymers or composites, for example, fiber reinforced, filled systems and liquid crystals, the orientation behavior needs to be described by more than one parameter. Orientation behavior, in general, is directly proportional to the material structure and orientation conditions. There are several common levels of structure that exist in a polymeric system, such as crystalline unit cell, lamellar thickness, domain size, spherulitic structures, oriented superstructures, phase separated domains in polymer blends and the like.

For example, in extruded polyethylene, the structure is a stacked folded chain lamellar structure. The orientation of the lamellae within the structure is along the machine direction, however the platelets are oriented perpendicular to the machine direction. The amorphous structure between the lamellae is generally not oriented. Mechanical properties of the material will be different when tested in different directions, for example, zero degree to the machine direction, forty-five degrees to the machine direction and ninety degrees to the machine direction. The elongation values are usually lowest when the material is stretched in machine direction. When stretched at forty-five degrees to the machine direction, shear deformation occurs of the lamellae and will provide higher elongation values. When stretched at ninety degrees to the machine direction, the material will exhibit highest elongation as the chain axis is unfolding.

When a polymer chain is oriented at an angle with respect to a given deformation axis, the orientation of the chain may be defined by Hermans orientation function, $f$, which varies from $1$, $-\frac{1}{2}$ and $0$ representing perfect orientation, perpendicular orientation, and random orientation along the axis, respectively. This applies mainly to uniaxially oriented systems. There are several techniques used to measure orientation such as birefringence, linear dichroism, wide angle x-ray scattering, polarized Raman scattering, polarized fluorescence, and nuclear magnetic resonance imaging or NMR.

The stents and/or other implantable medical devices of the current invention may be prepared from pure polymers, blends, and composites and may be used to prepare drug-loaded stents. The precursor material may be a tube or a film that is prepared by any suitable process, followed by laser cutting or any other suitable machining process. The precursor material may be used as prepared or can be modified by quenching, annealing, orienting or relaxing them under different conditions. Alternately, the laser cut stent may be used as prepared or may be modified by quenching, annealing, orienting or relaxing them under different conditions.

Mechanical Orientation

The effect of polymer orientation in a stent or device may improve the device performance including radial strength, recoil, and flexibility. Orientation may also vary the degradation time of the stent, so as desired, different sections of the stents may be oriented differently. Orientation may be along the axial and circumferential or radial directions as well as any other direction in the unit cell and flex connectors to enhance the performance of the stent in those respective directions. The orientation may be confined to only one direction (uniaxial), may be in two directions (biaxial) and/or multiple directions (multiaxial). The orientation may be introduced in a given material in different sequences, such as first applying axial orientation followed by radial orientation and vice versa. Alternately, the material may be oriented in both directions at the same time. Axial orientation may be applied by stretching along an axial or longitudinal direction in a given material such as tubes or films at temperatures usually above the glass transition temperature of the polymer. Radial or circumferential orientation may be applied by several different methods such as blowing the material by heated gas for example, nitrogen, or by using a balloon inside a mold. Alternately, a composite or sandwich structure may be formed by stacking layers of oriented material in different directions to provide anisotropic properties. Blow molding may also be used to induce biaxial and/or multiaxial orientation.

Orientation may be imparted to tubes, films or other geometries that are loaded with drugs in the range from about 1 to 50 percent. For example, drug loaded PLGA tubes prepared by any suitable process may be oriented at about 70 degrees C. to different amounts (for example, 50% to 300%) at different draw rates (for example, 100 mm/min to 1000 mm/min). The conditions to draw the material is important to prevent excessive fibrillation and void formation that may occur due to the presence of drug. If the draw temperature is increased to a higher value (for example, 90 degrees C.), then the orientation may not be retained as the temperature of orientation is much higher than the glass transition temperature of PLGA (about 60 degrees C.) and would cause relaxation of the polymer chains upon cooling.

Other methods of orienting the materials may include multi-stage drawing processes in which the material or device may be drawn at different draw rates at different temperatures before or after intermediate controlled annealing and relaxation steps. This method allows increasing the total draw ratio for a given material that is not otherwise possible in one-step drawing due to limitations of the material to withstand high draw ratio. These steps of orientation, annealing and relaxation will improve the overall strength and toughness of the material.

Figure 2:
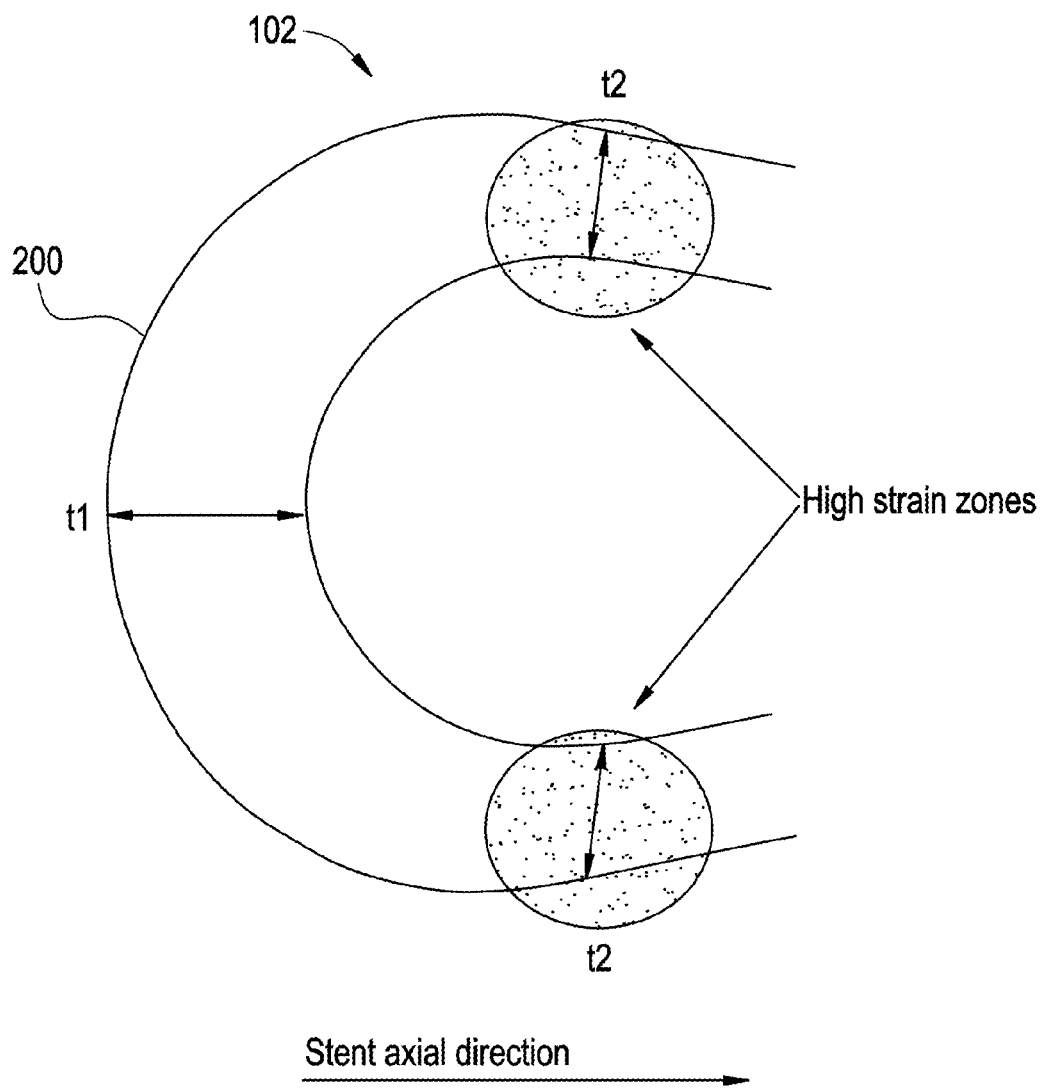
FIG. 2 is a representation of a section of hoop component of an exemplary stent that demonstrates two high strain zones to accommodate axial orientation in accordance with the present invention.

Referring to FIG. 2, there is illustrated a section 200 of a hoop component 102 formed from a polymeric material as described herein. As illustrated, the section 200 of the hoop component 102 is designed to have two first zones t2 and one second zone t1. The two zones, t2, are designed or configured to have a greater degree of polymer chain orientation compared to the one second zone, t1. The higher degree of polymer chain orientation can be achieved in zones t2 by drawing the precursor material in a direction along the longitudinal axis of the stent, or the axial direction. Additionally, orientation may also be achieved by methods described above. In the exemplary embodiment illustrated in FIG. 2, the t2 regions are thinner than the t1 region by design and because of this, the t2 regions are high strain zones compared to the t1 region. By optimizing the type and degree of polymer chain orientation and feature characteristics, the device performance characteristics may be enhanced. Performance characteristics for hoop components in a stent typically include radial strength, radial stiffness, and radial recoil. In addition, consideration should preferably be given to dynamic loads such as pulsatile motion.

Figure 3:
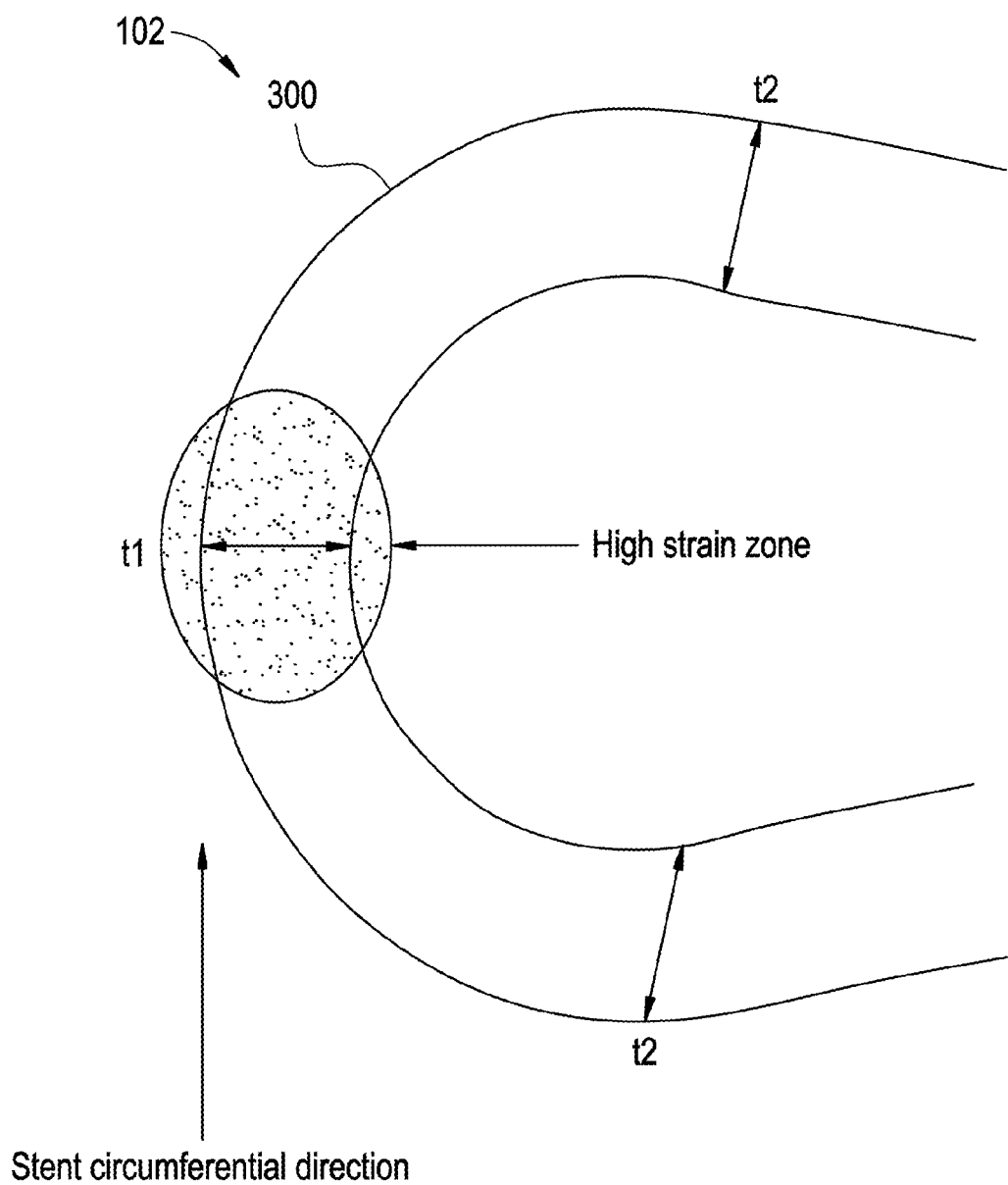
FIG. 3 is a representation of a section of hoop component of an exemplary stent that demonstrates one high strain zone to accommodate circumferential orientation in accordance with the present invention.

Referring to FIG. 3, there is illustrated a section 300 of a hoop component 102 formed from a polymeric material as described herein. As illustrated, the section 300 of the hoop component 102 is designed to have one first zone t1 and two second zones t2. The one zone, t1, is designed or configured to have a greater degree of polymer chain orientation compared to the two second zones, t2. The higher degree of polymer chain orientation may be achieved in zone t1 by drawing the precursor material in a direction along the radial or circumferential axis of the stent. Additionally, orientation may also be achieved by methods described above. In the exemplary embodiment illustrated in FIG. 3, the t1 region is thinner than the t2 regions by design and because of this, the t1 region is a high strain zone compared to the t2 regions. By optimizing the type and degree of polymer chain orientation and feature characteristics, the device performance characteristics may be enhanced. Performance characteristics for hoop components in a stent typically include radial strength, radial stiffness, and radial recoil. In addition, consideration should preferably be given to dynamic loads such as pulsatile motion.

Figure 4:
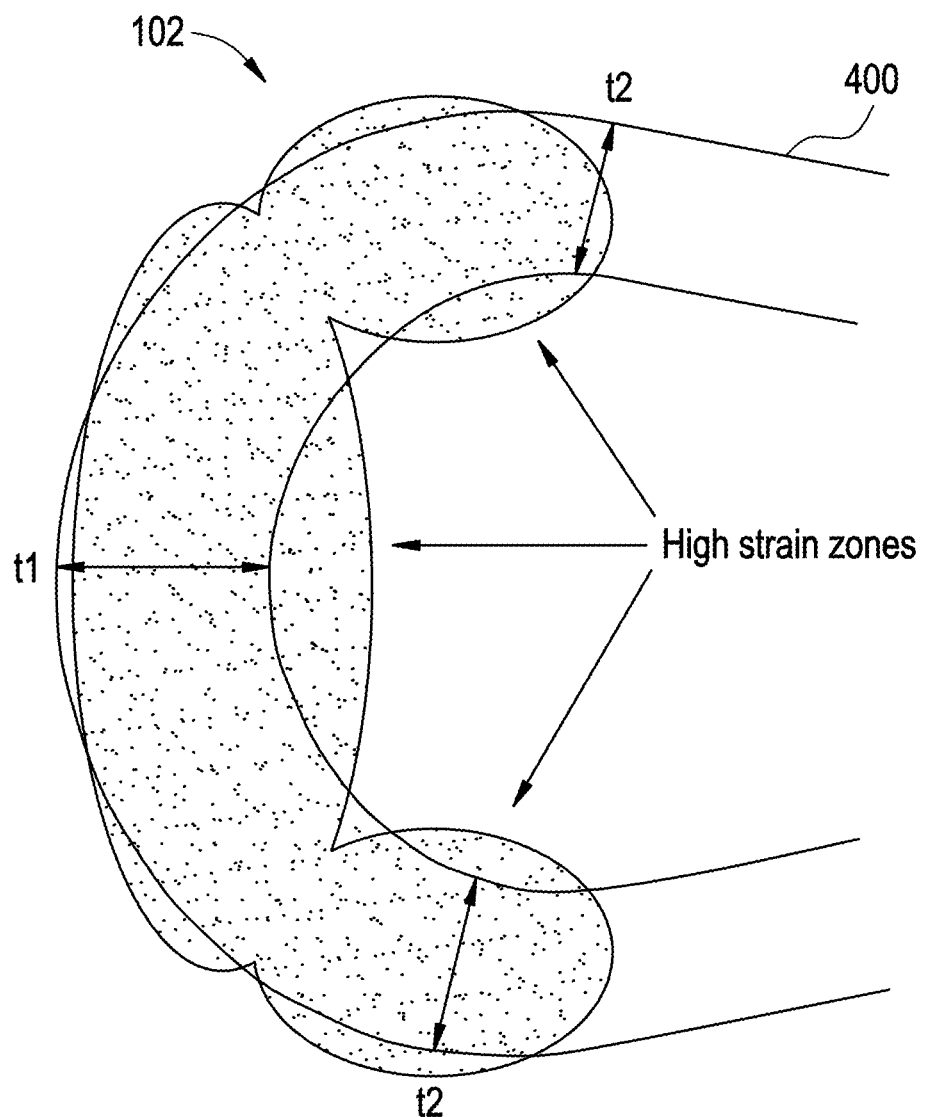
FIG. 4 is a representation of a section of hoop component of an exemplary stent that demonstrates three high strain zones to accommodate biaxial orientation in accordance with the present invention.

In addition, referring to FIG. 4, there is illustrated a section 400 of a hoop component 102 formed from a polymeric material as described herein. This drawing represents the combination of the polymer chain orientations illustrated in FIGS. 2 and 3. In other words, the degree of alignment in zones t1 and t2 may be substantially equal.

Figure 5:
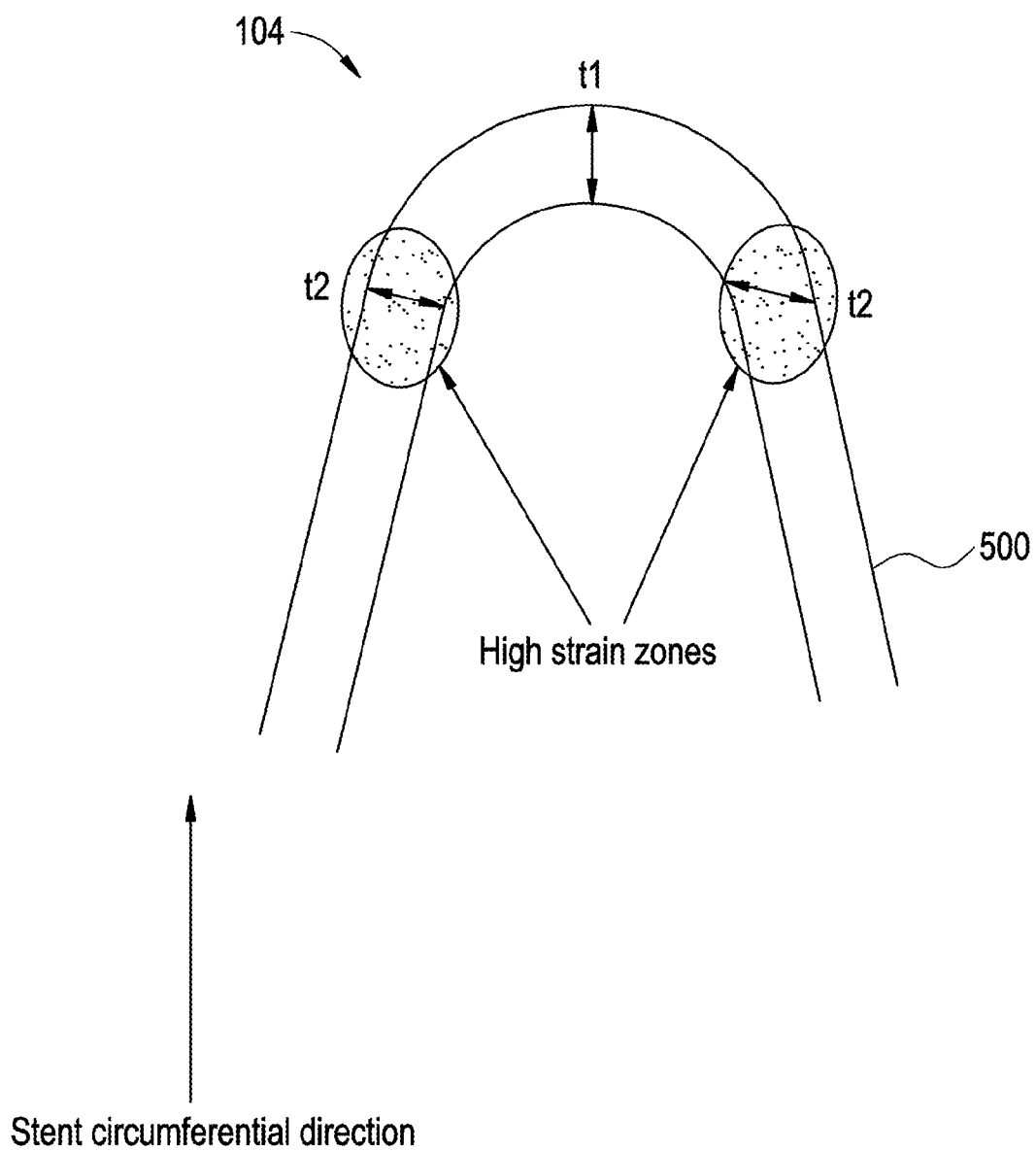
FIG. 5 is a representation of a section of flexible connector component of an exemplary stent that demonstrates two high strain zones to accommodate circumferential orientation in accordance with the present invention.

Referring to FIG. 5, there is illustrated a section 500 of a flexible connector 104 formed from a polymeric material as described herein. As illustrated, the section 500 of the flexible connector 104 is designed to have two first zones t2 and one second zone t1. The two zones, t2, are designed or configured to have a greater degree of polymer chain orientation compared to the one second zone, t1. The higher degree of polymer chain orientation may be achieved in zones t2 by drawing the precursor material in a direction along the radial or circumferential axis of the stent. Additionally, orientation may also be achieved by methods described above. In the exemplary embodiment illustrated in FIG. 5, the t2 regions are thinner than the t1 region by design and because of this, the t2 regions are high strain zones compared to the t1 region. By optimizing the type and degree of polymer chain orientation and feature characteristics, the device performance characteristics may be enhanced. Performance characteristics for flexible connector components in a stent are multiaxial and torsional flexibility in consideration of dynamic loading situations and foreshortening in consideration of deployment.

Figure 6:
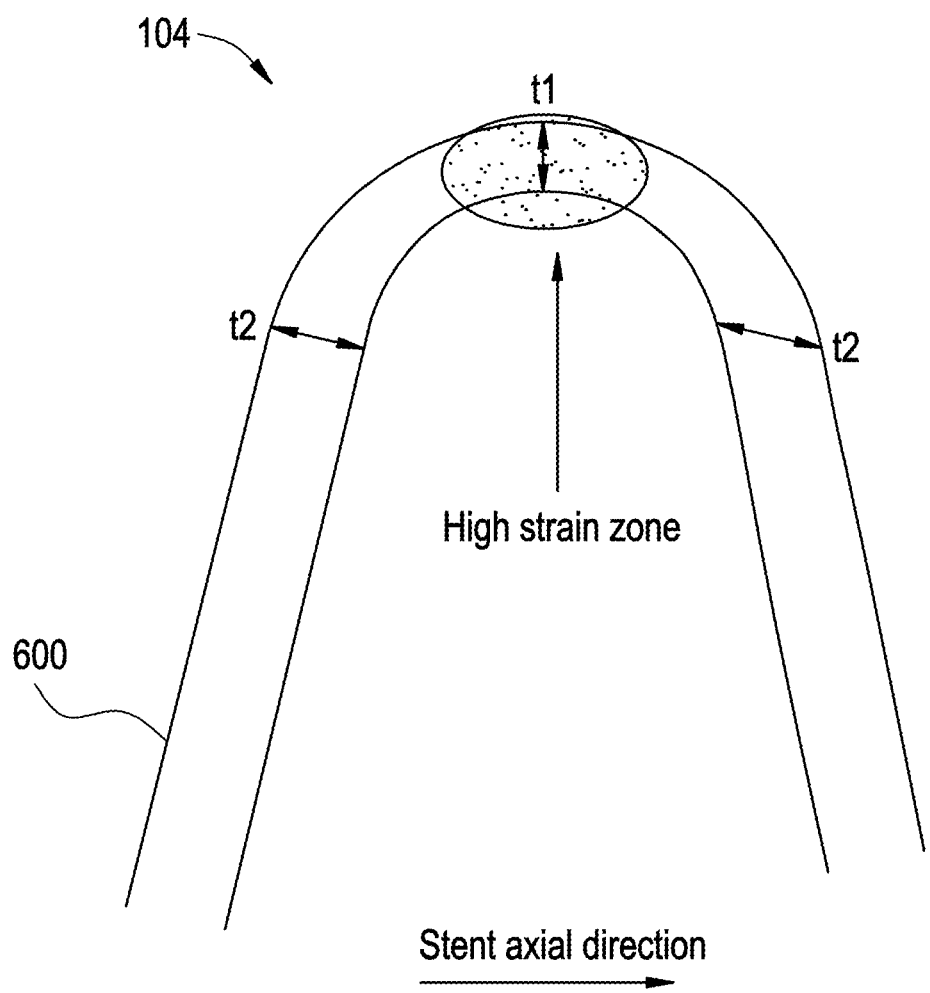
FIG. 6 is a representation of a section of flexible connector component of an exemplary stent that demonstrates one high strain zone to accommodate axial orientation in accordance with the present invention.

Referring to FIG. 6, there is illustrated a section 600 of a flexible connector 104 formed from a polymeric material as described herein. As illustrated, the section 600 of the flexible connector 104 is designed to have one first zone t1 and two second zones t2. The one zone, t1, is designed or configured to have a greater degree of polymer chain orientation compared to the two second zones, t2. The higher degree of polymer chain orientation may be achieved in zone t1 by drawing the precursor material in a direction along the longitudinal axis of the stent. Additionally, orientation may also be achieved by methods described above. In the exemplary embodiment illustrated in FIG. 6, the t1 region is a high strain zone compared to the t2 regions. By optimizing the type and degree of polymer chain orientation and feature characteristics, the device performance characteristics may be enhanced. Performance characteristics for flexible connector components in a stent are multiaxial and torsional flexibility in consideration of dynamic loading situations and foreshortening in consideration of deployment.

Figure 7:
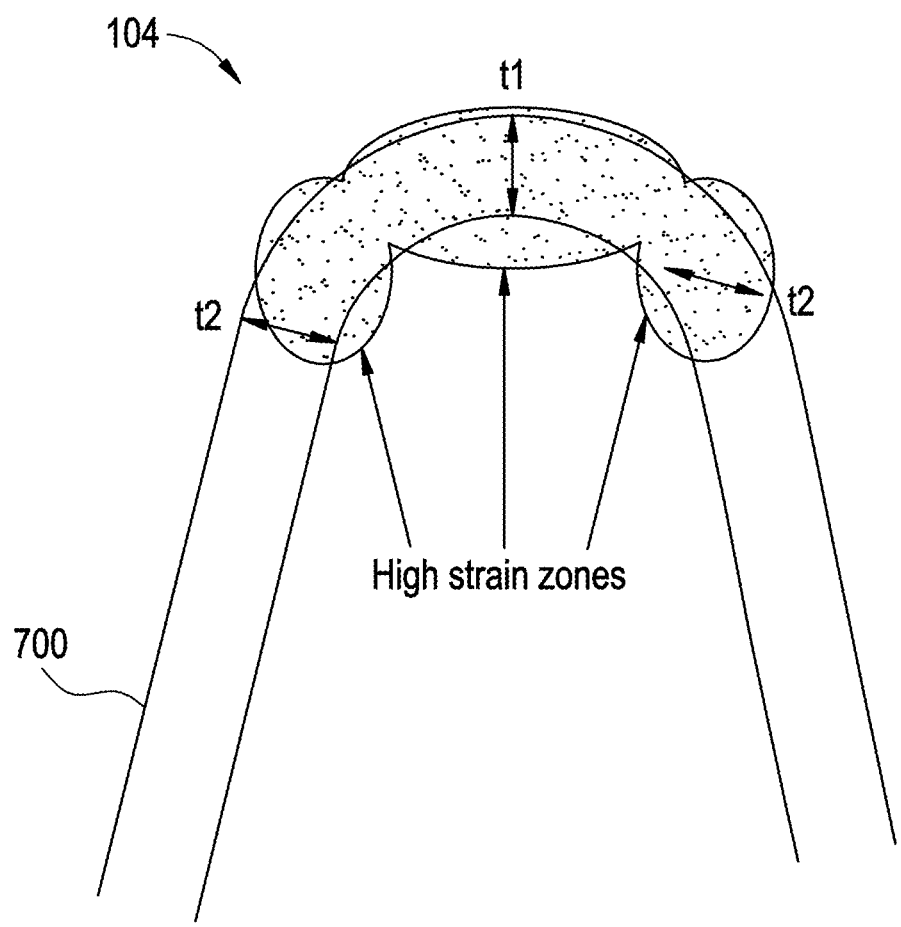
FIG. 7 is a representation of a section of flexible connector component of an exemplary stent that demonstrates three high strain zones to accommodate biaxial orientation in accordance with the present invention.

Referring to FIG. 7, there is illustrated a section 700 of a flexible connector 104 formed from a polymeric material as described herein. This drawing represents the combination of the polymer chain orientations illustrated in FIGS. 5 and 6. In other words, the degree of alignment in zones t1 and t2 may be substantially equal.

To the skilled artisan, there are a multitude of design considerations that will determine which configuration is preferred to achieve optimal stent performance. The figures above merely illustrate a few possibilities. It is appropriate to consider acute and chronic stent performance attributes in order to optimize the design and material combination. One of these factors includes the design of the flexible connector elements. For example, if the flexible connector joins the radial hoops at the apex of the radial arc, the designer may choose the longitudinal component of the radial hoop to contain the high strain region. Optimization of the material and the design would thus result in the preferential longitudinal orientation of the polymer chains. Alternately, if the flexible connectors join the radial hoops at the ends of the radial arcs or in the radial strut sections, the designer may choose the apex of the radial arc to contain the high strain region. Accordingly, in this design optimization of the material and the design would thus result in the preferential circumferential orientation of the polymer chains.

Additionally, if loads on the flexible connector align to the longitudinally oriented elements of the flexible connector, then optimization of the material and design would result in the preferential longitudinal orientation of the polymer chains. Similarly, if loads on the flexible connector align to the circumferentially oriented elements of the flexible connector, then optimization of the material and design would result in the preferential circumferential orientation of the polymer chains.

The above descriptions are merely illustrative and should not be construed to capture all consideration in decisions regarding the optimization of the design and material orientation.

It is important to note that although specific configurations are illustrated and described, the principles described are equally applicable to any configurations of hoop and flexible connector designs. In addition, the axes of alignment may not correspond to a single direction, for example longitudinally or radially, but rather a combination of the two.

Polymeric Materials

Polymeric materials may be broadly classified as synthetic, natural and/or blends thereof. Within these broad classes, the materials may be defined as biostable or biodegradable. Examples of biostable polymers include polyolefins, polyamides, polyesters, fluoropolymers, and acrylics. Examples of natural polymers include polysaccharides and proteins.

The drug delivery devices according to the systems and methods of the present invention may be disease specific, and may be designed for local or regional therapy, or a combination thereof. They may be used to treat coronary and peripheral diseases such as vulnerable plaque, restenosis, bifurcated lesions, superficial femoral artery, below the knee, saphenous vein graft, arterial tree, small and tortuous vessels, and diffused lesions. The drugs or other agents delivered by the drug delivery devices according to the systems and methods of the present invention may be one or more drugs, bio-active agents such as growth factors or other agents, or combinations thereof. The drugs or other agents of the device are ideally controllably released from the device, wherein the rate of release depends on either or both of the degradation rates of the bioabsorbable polymers comprising the device and the nature of the drugs or other agents. The rate of release can thus vary from minutes to years as desired.

Bioabsorobable and/or biodegradable polymers consist of bulk and surface erodable materials. Surface erosion polymers are typically hydrophobic with water labile linkages. Hydrolysis tends to occur fast on the surface of such surface erosion polymers with no water penetration in bulk. The initial strength of such surface erosion polymers tends to be low however, and often such surface erosion polymers are not readily available commercially. Nevertheless, examples of surface erosion polymers include polyanhydrides such as poly (carboxyphenoxy hexane-sebacic acid), poly (fumaric acid-sebacic acid), poly (carboxyphenoxy hexane-sebacic acid), poly (imide-sebacic acid)(50-50), poly (imide-carboxyphenoxy hexane) (33-67), and polyorthoesters (diketene acetal based polymers).

Bulk erosion polymers, on the other hand, are typically hydrophilic with water labile linkages. Hydrolysis of bulk erosion polymers tends to occur at more uniform rates across the polymer matrix of the device. Bulk erosion polymers exhibit superior initial strength and are readily available commercially.

Examples of bulk erosion polymers include poly ($\alpha$-hydroxy esters) such as poly (lactic acid), poly (glycolic acid), poly (caprolactone), poly (p-dioxanone), poly (trimethylene carbonate), poly (oxaesters), poly (oxaamides), and their co-polymers and blends. Some commercially readily available bulk erosion polymers and their commonly associated medical applications include poly (dioxanone) [PDS® suture available from Ethicon, Inc., Somerville, N.J.], poly (glycolide) [Dexon® sutures available from United States Surgical Corporation, North Haven, Conn.], poly (lactide)-PLLA [bone repair], poly (lactide/glycolide) [Vicryl® (10/90) and Panacryl® (95/5) sutures available from Ethicon, Inc., Somerville, N.J.], poly (glycolide/caprolactone (75/25) [Monocryl® sutures available from Ethicon, Inc., Somerville, N.J.], and poly (glycolide/trimethylene carbonate) [Maxon® sutures available from United States Surgical Corporation, North Haven, Conn.].

Other bulk erosion polymers are tyrosine derived poly amino acid [examples: poly (DTH carbonates), poly (arylates), and poly (imino-carbonates)], phosphorous containing polymers [examples: poly (phosphoesters) and poly (phosphazenes)], poly (ethylene glycol) [PEG] based block co-polymers [PEG-PLA, PEG-poly (propylene glycol), PEG-poly (butylene terephthalate)], poly ($\alpha$-malic acid), poly (ester amide), and polyalkanoates [examples: poly (hydroxybutyrate (HB) and poly (hydroxyvalerate) (HV) co-polymers].

Of course, the devices may be made from combinations of surface and bulk erosion polymers in order to achieve desired physical properties and to control the degradation mechanism. For example, two or more polymers may be blended in order to achieve desired physical properties and device degradation rate. Alternately, the device may be made from a bulk erosion polymer that is coated with a surface erosion polymer. The drug delivery device may be made from a bulk erosion polymer that is coated with a drug containing a surface erosion polymer. For example, the drug coating may be sufficiently thick that high drug loads may be achieved, and the bulk erosion polymer may be made sufficiently thick that the mechanical properties of the device are maintained even after all of the drug has been delivered and the surface eroded.

Shape memory polymers may also be used. Shape memory polymers are characterized as phase segregated linear block co-polymers having a hard segment and a soft segment. The hard segment is typically crystalline with a defined melting point, and the soft segment is typically amorphous with a defined glass transition temperature. The transition temperature of the soft segment is substantially less than the transition temperature of the hard segment in shape memory polymers. A shape in the shape memory polymer is memorized in the hard and soft segments of the shape memory polymer by heating and cooling techniques. Shape memory polymers may be biostable and bioabsorbable. Bioabsorbable shape memory polymers are relatively new and comprise thermoplastic and thermoset materials. Shape memory thermoset materials may include poly (caprolactone) dimethylacrylates, and shape memory thermoplastic materials may include poly (caprolactone) as the soft segment and poly (glycolide) as the hard segment.

The selection of the bioabsorbable polymeric material used to comprise the drug delivery device according to the invention is determined according to many factors including, for example, the desired absorption times and physical properties of the bioabsorbable materials, and the geometry of the drug delivery device.

Properties/Blends

Toughness of a system is the mechanical energy or work required to induce failure, and depends on testing conditions such as temperatures and loading rates. Toughness is the area under the engineering stress-strain curve, and is therefore an ultimate property for a given material. For this reason, it is important to obtain data from a large population of specimens in order to achieve accurate toughness values. Toughness of polymers may fall in to several different categories. A material that is hard and brittle will have high modulus and low strain at break values and will therefore have low toughness, and a material that is hard and tough will have high modulus and high strain at break values and will therefore have high toughness. Similarly, a material that is soft and weak will have low modulus and low strain at break values and will have low toughness, and a material that is soft and tough will have low modulus and high strain at break values and will have high toughness values. Ideally, it is desirable to have a material with high toughness that has high modulus and high strain at break or ultimate strain values for a vascular device such as drug loaded stent.

Mechanical hysteresis is the energy that is lost during cyclic deformation, and is an important factor in dynamic loading applications of polymers such as in vascular stents. Since polymers are viscoelastic materials, they all exhibit mechanical hysteresis unlike in elastic materials where there is no energy loss during cyclic deformation. The amount or percent of mechanical hysteresis depends on the type of polymers. For example, it is possible that elastomers will have low percent mechanical hysteresis compared to a stiff and brittle non-elastomeric material. Also, non-elastomeric materials may also have permanent set after removing load from its deformed state.

In order to provide materials with high toughness, such as is often required for orthopedic implants, sutures, stents, grafts and other medical applications including drug delivery devices, the bioabsorbable polymeric materials may be modified to form composites or blends thereof. Such composites or blends may be achieved by changing either the chemical structure of the polymer backbone, or by creating composite structures by blending them with different polymers and plasticizers.

The addition of plasticizers, which are generally low molecular weight materials, or a soft (lower glass transition temperature) miscible polymer, will depress the glass transition temperature of the matrix polymer system. In general, these additional materials that are used to modify the underlying bioabsorbable polymer should preferably be miscible with the main matrix polymer system to be effective.

In accordance with the present invention, the matching of a suitable polymer or blends thereof and plasticizer or mixtures thereof to form a blend for the preparation of a drug loaded stent or device, or a stent or device with no drug is important in achieving desirable properties. Combining the polymers and plasticizers is accomplished by matching the solubility parameters of the polymer component and plasticizer component within a desired range. Solubility parameters of various materials and methods of calculating the same are known in the art. The total solubility parameter of a compound is the sum of the solubility parameter values contributed by dispersive forces, hydrogen bonding forces and polar forces. A polymer will dissolve in a plasticizer or be plasticized if either the total solubility parameter or one or more of the disperse forces, polar forces, and hydrogen bonding forces for each of the polymer and plasticizer are similar.

Free volume is the space between molecules, and it increases with increased molecular motion. Accordingly, a disproportionate amount of free volume is associated with chain end groups in a polymer system. Increasing the concentration of chain end groups increases the free volume. The addition of flexible side chains in to macromolecules therefore increases the free volume. All of these effects may be used for internal plasticization, and free volume is spatially fixed with regard to the polymer molecule. However, the addition of a small molecule affects the free volume of large macromolecules at any location by the amount of material added, which is known as external plasticization. The size and shape of the molecule that is added and the nature of its atoms and groups of atoms (i.e., non-polar, polar, hydrogen bonding, etc) determine how it functions as a plasticizer. The normal effect of increasing the free volume of a polymer is that it is plasticized (i.e., the glass transition temperature is lowered, the modulus and tensile strength decreases, and elongation at break and toughness increases). However, the freedom of movement afforded by the plasticizer also permits the polymer molecules to associate tightly with each other. In general, free volume is based on the principle that a suitable plasticizer increases the free volume of the polymer. An increase in free volume of the polymer increases the mobility of the polymer and therefore extent of plasticization. Thus, if more plasticization is desired, the amount of the plasticizer may be increased.

Figure 8:
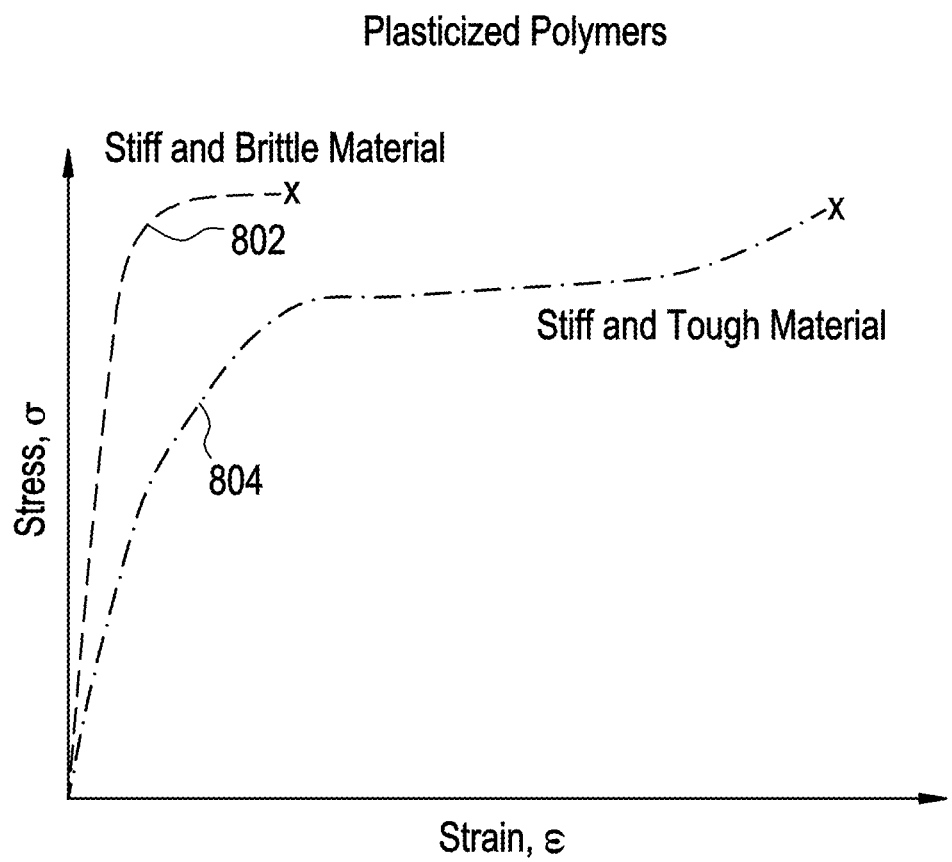
FIG. 8 is a schematic representation of a stress-strain curve of a stiff and brittle material and a plasticized material in accordance with the present invention.

FIG. 8 is a schematic representation of the stress-strain behavior of a plasticized stiff and brittle material, represented by curve 804. The stiff and brittle polymeric material, represented by curve 802, is altered by the addition of a plasticizer. Stiff material has a higher modulus and low strain at break values with low toughness as the area under the curve is small. The addition of a plasticizer makes the stiff and brittle material a stiff and tough material. In other words, the addition of a plasticizer will lower the modulus to some extent but will increase the ultimate strain value thereby making the plasticized material tougher. As stated above, curve 804 represents the blend of a stiff and brittle polymer with a plasticizer resulting in a material with a modified stress-strain curve. The amount of change in modulus and toughness depends on the amount of plasticizer in the polymer. In general, the higher the amount of plasticizer, the lower the modulus and the higher the toughness values.

Plasticizers that are added to the matrix of bioabsorbable polymer materials will make the device more flexible and typically reduces the processing temperatures in case of processing materials in melt. The plasticizers are added to the bioabsorbable materials of the device prior to or during processing thereof. As a result, degradation of drugs incorporated into the bioabsorbable materials having plasticizers added thereto during processing is further minimized.

Plasticizers or mixtures thereof suitable for use in the present invention may be selected from a variety of materials including organic plasticizers and those like water that do not contain organic compounds. Organic plasticizers include but not limited to, phthalate derivatives such as dimethyl, diethyl and dibutyl phthalate; polyethylene glycols with molecular weights preferably from about 200 to 6,000, glycerol, glycols such as polypropylene, propylene, polyethylene and ethylene glycol; citrate esters such as tributyl, triethyl, triacetyl, acetyl triethyl, and acetyl tributyl citrates, surfactants such as sodium dodecyl sulfate and polyoxymethylene (20) sorbitan and polyoxyethylene (20) sorbitan monooleate, organic solvents such as 1,4-dioxane, chloroform, ethanol and isopropyl alcohol and their mixtures with other solvents such as acetone and ethyl acetate, organic acids such as acetic acid and lactic acids and their alkyl esters, bulk sweeteners such as sorbitol, mannitol, xylitol and lycasin, fats/oils such as vegetable oil, seed oil and castor oil, acetylated monoglyceride, triacetin, sucrose esters, or mixtures thereof. Preferred organic plasticizers include citrate esters; polyethylene glycols and dioxane.

Citrate esters are renewable resource derivatives derived from citric acid, a tribasic monohydroxy acid (2-hydroxy-1, 2, 3-propanetricarboxylic acid), $C_6H_8O_7$, and a natural constituent and common metabolite of plants and animals. They are non-toxic and have been used as plasticizers with a variety of different polymers. Different grades of citrate esters are available from Morflex, Inc. Typical molecular weights, boiling points, solubility in water and solubility parameters are 270 to 400 g/mole; 125 to 175 degrees C.; <0.1 to 6.5 g/100 mL and 18 to 20 $(J/cm^3)^{1/2}$, respectively. Molecular weight has a strong influence on all the properties. As it increases, boiling point increases and the molecule becomes less polar as the water solubility and solubility parameters decreases.

Polyethylene glycols are water-soluble and are available in molecular weights ranging from 200 to 20,000 g/mole. The solubility decreases with increasing molecular weight. These materials are also soluble in polar organic solvents such as chloroform and acetone. These polymers are readily available from several suppliers.

Solubility parameter value of solvents such as dioxane and chloroform is about 20 and 19 $MPa^{1/2}$, respectively, and these are considered as some of the good solvents for bioabsorbable materials such as poly (lactic acid-co-glycolic acid). So, it may be assumed that the solubility parameter for these materials should be close to those of the solvents.

Citrate ester plasticizers may be added to bioabsorbable polymers in the range from 1 to 50 percent, preferably from 1 to 35 percent and more preferably from 1 to 20 percent by weight in the presence of drug and/or radiopaque agent. The polymers may be selected from poly (lactic acid-co-glycolic acid) (95/5 to 85/15 ratio), the radiopaque agent is barium sulfate (preferred range is 10 percent to 50 percent) and the drug is sirolimus (preferred range is 1 percent to 30 percent). These may be converted to tubes or films utilizing any suitable process. The elongation at break values for the polymer system increases to above 20 percent with the addition of 1 to 20 percent of the plasticizer. This exhibits significant increase in toughness and is very favorable for high strain balloon expandable stent designs.

Polymer blends are commonly prepared to achieve the desired final polymer properties. In accordance with the present invention, polymer blends are prepared to increase the elongation at break values or ultimate strain and thereby improving the toughness of the material that will be used to prepare vascular devices such as stents. Selection of the materials is important in order to achieve high toughness values of the matrix polymer. Matching solubility parameters and increase in free volume is important for the polymer blends to achieve the desired performance. The main difference between adding a plasticizer and a polymer to the matrix polymer is the difference in their molecular weights. As mentioned earlier, plasticizers have lower molecular weight compared to a polymeric additive. However, some low molecular weight polymers may also be used as a plasticizer. It is possible to achieve high toughness values by adding low amounts of plasticizer compared to a polymeric additive. Relatively high molecular weight material has been used as the matrix material for the present invention. For example, the molecular weight (weight average) of PLGA resins may be above 300,000 Daltons. Thermodynamically, molecular weight plays a big role in miscibility of polymer systems. There is higher miscibility between polymer and a low molecular weight additive compared to a high molecular weight additive. As mentioned earlier, the addition of a miscible polymer will lower glass transition temperature, decrease modulus and tensile strength with an increase in the toughness values.

Figure 9:
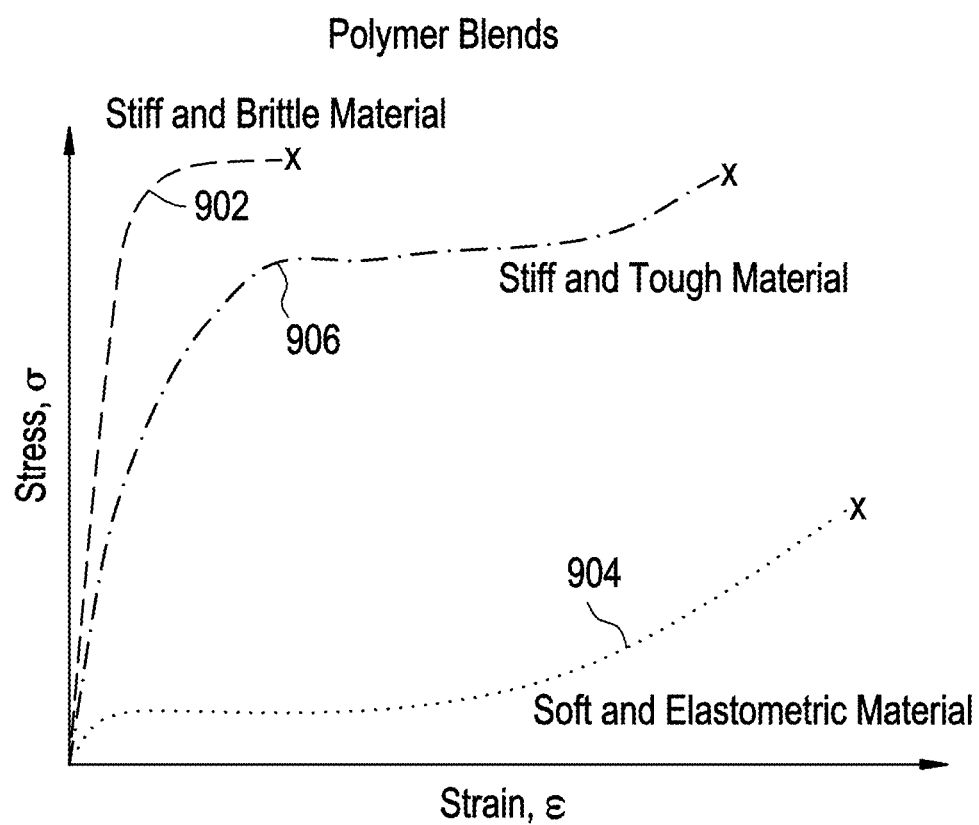
FIG. 9 is a schematic representation of a stress-strain curve of a stiff and brittle material, a soft and elastomeric material and a blend of the stiff and elastomeric material in accordance with the present invention.

FIG. 9 is a schematic representation of the stress-strain behavior of a stiff and brittle material with high modulus and low strain at break values, i.e., low toughness, as represented by curve 902 with a soft and elastomeric material with low modulus and relatively high strain at break values, as represented by curve 904 and the resultant polymer blend prepared from these two materials, as represented by curve 906, that will provide a relatively stiff material with high ultimate strain values, i.e., high toughness. The amount of change in modulus, strength and strain at break values depends on the amount of the polymeric additive in the matrix polymer. In general, the polymers are miscible or compatible at lower levels of the additive (for example <50 percent by weight) beyond which they become phase separated and the physical properties may begin to deteriorate. However, it is important to note that it is possible to achieve desirable compatibility between the phase-separated polymers through the addition of bioabsorbable compatibilizers.

As an example of producing a composite or blended material, blending a stiff polymer such as poly (lactic acid), poly (glycolide) and poly (lactide-co-glycolide) copolymers with a soft and elastomeric polymer such as poly (caprolactone) and poly (dioxanone) tends to produce a material with high toughness and high stiffness. An elastomeric co-polymer may also be synthesized from a stiff polymer and a soft polymer in different ratios. For example, poly (glycolide) or poly (lactide) may be copolymerized with poly (caprolactone) or poly (dioxanone) to prepare poly (glycolide-co-caprolactone) or poly (glycolide-co-dioxanone) and poly (lactide-co-caprolactone) or poly (lactide-co-dioxanone) copolymers. These elastomeric copolymers may then be blended with stiff materials such as poly (lactide), poly (glycolide) and poly (lactide-co-glycolide) copolymers to produce a material with high toughness and ductility. Alternatively, terpolymers may also be prepared from different monomers to achieve desired properties. For example, poly (caprolactone-co-glycolide-co-lactide) may be prepared in different ratios.

Preferred materials for the matrix polymer are poly (lactic acid-co-glycolic acid) (95/5 and 85/15), which are usually stiff and brittle. Preferred soft and elastomeric materials for the polymers that are added to the matrix polymer are poly (caprolactone); poly (dioxanone); copolymers of poly (caprolactone) and poly (dioxanone); and co-polymers of poly (caprolactone) and poly (glycolide). The ratios of the monomer content for the copolymers may range from about 95/5 to about 5/95. Preferably, the ratios are about 95/5 to about 50/50 for poly (caprolactone)/poly (dioxanone) copolymer, and from about 25/75 to about 75/25 for poly (caprolactone)/poly (glycolide) copolymers. The addition of these polymers to the matrix polymer may vary from 1 percent to 50 percent, and more preferably from 5 to 35 percent (wt/wt). These blends should preferably comprise a high amount of drug (1 to 30 percent) such as sirolimus and radiopaque agents (10 to 50 percent) such as barium sulfate, and may be prepared using any suitable process.

In addition to increasing the toughness values with the addition of the soft polymers, the absorption time may also be modified. For example, the blend of PLGA with polycaprolactone will increase the total absorption time of the blended material as polycaprolactone degrades slower than PLGA. The total absorption may be reduced for PLGA by blending it with faster degrading materials such as poly (dioxanone) and their copolymers with poly (glycolide) and poly (lactide); and copolymers of poly (glycolide) such as poly (caprolactone-co-glycolide).

Reinforced composites may also be prepared by blending high modulus PGA fibers or bioabsorbable particulate fillers with PLGA to form composites in the presence of the plasticizers or soft materials to improve the modulus of the final material.

It is important to note that the drug or therapeutic agent, in sufficient concentration, may be used as an additive for modifying the polymer properties. In other words, the drug or therapeutic agent may be utilized as part of the blend, rather than as a material affixed to a base material, similar to the blends described herein to achieve the desired end product properties in addition to providing a therapeutic effect.

Additives

Because visualization of the device as it is implanted in the patient is important to the medical practitioner for locating the device, radiopaque materials may be added to the device.

The radiopaque materials may be added directly to the matrix of bioabsorbable materials comprising the device during processing thereof resulting in fairly uniform incorporation of the radiopaque materials throughout the device. Alternately, the radiopaque materials may be added to the device in the form of a layer, a coating, a band or powder at designated portions of the device depending on the geometry of the device and the process used to form the device. Coatings may be applied to the device in a variety of processes known in the art such as, for example, chemical vapor deposition (CVD), physical vapor deposition (PVD), electroplating, high-vacuum deposition process, microfusion, spray coating, dip coating, electrostatic coating, or other surface coating or modification techniques. Such coatings sometimes have less negative impact on the physical characteristics (eg., size, weight, stiffness, flexibility) and performance of the device than do other techniques. Preferably, the radiopaque material does not add significant stiffness to the device so that the device may readily traverse the anatomy within which it is deployed. The radiopaque material should be biocompatible with the tissue within which the device is deployed. Such biocompatibility minimizes the likelihood of undesirable tissue reactions with the device. Inert noble metals such as gold, platinum, iridium, palladium, and rhodium are well-recognized biocompatible radiopaque materials. Other radiopaque materials include barium sulfate ($BaSO_4$), bismuth subcarbonate [$(BiO)_2CO_3$] and bismuth oxide. Preferably, the radiopaque materials adhere well to the device such that peeling or delamination of the radiopaque material from the device is minimized, or ideally does not occur. Where the radiopaque materials are added to the device as metal bands, the metal bands may be crimped at designated sections of the device. Alternately, designated sections of the device may be coated with a radiopaque metal powder, whereas other portions of the device are free from the metal powder.

The bioabsorbable polymer materials comprising the drug delivery device according to the invention may include radiopaque additives added directly thereto during processing of the matrix of the bioabsorbable polymer materials to enhance the radiopacity of the device. The radiopaque additives may include inorganic fillers, such as barium sulfate, bismuth subcarbonate, bismuth oxides and/or iodine compounds. The radiopaque additives may instead include metal powders such as tantalum, tungsten or gold, or metal alloys having gold, platinum, iridium, palladium, rhodium, a combination thereof, or other materials known in the art. The particle size of the radiopaque materials may range from nanometers to microns, preferably from less than or equal to 1 micron to about 5 microns, and the amount of radiopaque materials may range from 0-99 percent (wt percent).

Because the density of the radiopaque additives is typically very high where the radiopaque materials are distributed throughout the matrix of bioabsorbable materials, dispersion techniques are preferably employed to distribute the radiopaque additives throughout the bioabsorbable materials as desired. Such techniques include high shear mixing, surfactant and lubricant additions, viscosity control, surface modification of the additive, and other particle size, shape and distribution techniques. In this regard, it is noted that the radiopaque materials may be either uniformly distributed throughout the bioabsorbable materials of the device, or may be concentrated in sections of the device so as to appear as markers similar to as described above.

The local delivery of therapeutic agent/therapeutic agent combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices that serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, including stents, stent-grafts and other devices for repairing aneurysims, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any other type of medical device may be coated in some fashion with a drug or drug combination, which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagines); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine and cytarabine) purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory; such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalec), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors, antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As described herein various drugs or agents may be incorporated into the medical device by a number of mechanisms, including blending it with the polymeric materials or affixing it to the surface of the device. Different drugs may be utilized as therapeutic agents, including sirolimus, or rapamycin, heparin, everolimus, tacrolimus, paclitaxel, cladribine as well as classes of drugs such as statins. These drugs and/or agents may be hydrophilic, hydrophobic, lipophilic and/or lipophobic.

Rapamycin is a macrocyclic triene antibiotic produced by *Steptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endotheliazation of the vessel walls.

Rapamycin reduces vascular hyperplasic by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

As used herein, rapamycin includes rapamycin and all analogs, derivatives and conjugates that bind to FKBP12, and other immunophilins and possesses the same pharmacologic properties as rapamycin including inhibition of TOR.

The amount of drugs or other agents incorporated within the drug delivery device according to the systems and methods of the present invention may range from about 0 to 99 percent (percent weight of the device). The drugs or other agents may be incorporated into the device in different ways. For example, the drugs or other agents may be coated onto the device after the device has been formed, wherein the coating is comprised of bioabsorbable polymers into which the drugs or other agents are incorporated. Alternately, the drugs or other agents may be incorporated into the matrix of bioabsorbable materials comprising the device. The drugs or agents incorporated into the matrix of bioabsorbable polymers may be in an amount the same as, or different than, the amount of drugs or agents provided in the coating techniques discussed earlier if desired. These various techniques of incorporating drugs or other agents into, or onto, the drug delivery device may also be combined to optimize performance of the device, and to help control the release of the drugs or other agents from the device.

Where the drug or agent is incorporated into the matrix of bioabsorbable polymers comprising the device, for example, the drug or agent will release by diffusion and during degradation of the device. The amount of drug or agent released by diffusion will tend to release for a longer period of time than occurs using coating techniques, and may often more effectively treat local and diffuse lesions or conditions thereof. For regional drug or agent delivery such diffusion release of the drugs or agents is effective as well. Polymer compositions and their diffusion and absorption characteristics will control drug elution profile for these devices. The drug release kinetics will be controlled by drug diffusion and polymer absorption. Initially, most of the drug will be released by diffusion from the device surfaces and bulk and will then gradually transition to drug release due to polymer absorption. There may be other factors that will also control drug release. If the polymer composition is from the same monomer units (e.g., lactide; glycolide), then the diffusion and absorption characteristics will be more uniform compared to polymers prepared from mixed monomers. Also, if there are layers of different polymers with different drug in each layer, then there will be more controlled release of drug from each layer. There is a possibility of drug present in the device until the polymer fully absorbs thus providing drug release throughout the device life cycle.

The drug delivery device according to the systems and methods of the present invention preferably retains its mechanical integrity during the active drug delivery phase of the device. After drug delivery is achieved, the structure of the device ideally disappears as a result of the bioabsorption of the materials comprising the device. The bioabsorbable materials comprising the drug delivery device are preferably biocompatible with the tissue in which the device is implanted such that tissue interaction with the device is minimized even after the device is deployed within the patient. Minimal inflammation of the tissue in which the device is deployed is likewise preferred even as degradation of the bioabsorbable materials of the device occurs. In order to provide multiple drug therapy, enriched or encapsulated drug particles or capsules may be incorporated in the polymer matrix. Some of these actives may provide different therapeutic benefits such as anti-inflammatory, anti-thrombotic; etc.

In accordance with another exemplary embodiment, the stents described herein, whether constructed from metals or polymers, may be utilized as therapeutic agents or drug delivery devices wherein the drug is affixed to the surface of the device. The metallic stents may be coated with a biostable or bioabsorbable polymer or combinations thereof with the therapeutic agents incorporated therein. Typical material properties for coatings include flexibility, ductility, tackiness, durability, adhesion and cohesion. Biostable and bioabsorbable polymers that exhibit these desired properties include methacrylates, polyurethanes, silicones, poly (vinyl acetate), poly (vinyl alcohol), ethylene vinyl alcohol, poly (vinylidene fluoride), poly (lactic acid), poly (glycolic acid), poly (caprolactone), poly (trimethylene carbonate), poly (dioxanone), polyorthoester, polyanhydrides, polyphosphoester, polyaminoacids as well as their copolymers and blends thereof.

In addition to the incorporation of therapeutic agents, the surface coatings may also include other additives such as radiopaque constituents, chemical stabilizers for both the coating and/or the therapeutic agent, radioactive agents, tracing agents such as radioisotopes such as tritium (i.e. heavy water) and ferromagnetic particles, and mechanical modifiers such as ceramic microspheres as will be described in greater detail subsequently. Alternatively, entrapped gaps may be created between the surface of the device and the coating and/or within the coating itself. Examples of these gaps include air as well as other gases and the absence of matter (i.e. vacuum environment). These entrapped gaps may be created utilizing any number of known techniques such as the injection of microencapsulated gaseous matter.

As described above, different drugs may be utilized as therapeutic agents, including sirolimus, heparin, everolimus, tacrolimus, paclitaxel, cladribine as well as classes of drugs such as statins. These drugs and/or agents may be hydrophilic, hydrophobic, lipophilic and/or lipophobic. The type of agent will play a role in determining the type of polymer. The amount of the drug in the coating may be varied depending on a number of factors including, the storage capacity of the coating, the drug, the concentration of the drug, the elution rate of the drug as well as a number of additional factors. The amount of drug may vary from substantially zero percent to substantially one hundred percent. Typical ranges may be from about less than one percent to about forty percent or higher. Drug distribution in the coating may be varied. The one or more drugs may be distributed in a single layer, multiple layers, single layer with a diffusion barrier or any combination thereof.

Different solvents may be used to dissolve the drug/polymer blend to prepare the coating formulations. Some of the solvents may be good or poor solvents based on the desired drug elution profile, drug morphology and drug stability.

There are several ways to coat the stents that are disclosed in the prior art. Some of the commonly used methods include spray coating; dip coating; electrostatic coating; fluidized bed coating; and supercritical fluid coatings.

Some of the processes and modifications described herein that may be used will eliminate the need for polymer to hold the drug on the stent. Stent surfaces may be modified to increase the surface area in order to increase drug content and tissue-device interactions. Nanotechnology may be applied to create self-assembled nanomaterials that can contain tissue specific drug containing nanoparticles. Microstructures may be formed on surfaces by microetching in which these nanoparticles may be incorporated. The microstructures may be formed by methods such as laser micromachining, lithography, chemical vapor deposition and chemical etching. Microstructures may be added to the stent surface by vapor deposition techniques. Microstructures have also been fabricated on polymers and metals by leveraging the evolution of micro electromechanical systems (MEMS) and microfluidics. Examples of nanomaterials include carbon nanotubes and nanoparticles formed by sol-gel technology. Therapeutic agents may be chemically or physically attached or deposited directly on these surfaces. Combination of these surface modifications may allow drug release at a desired rate. A top-coat of a polymer may be applied to control the initial burst due to immediate exposure of drug in the absence of polymer coating.

As described above, polymer stents may contain therapeutic agents as a coating, e.g. a surface modification. Alternatively, the therapeutic agents may be incorporated into the stent structure, e.g. a bulk modification that may not require a coating. For stents prepared from biostable and/or bioabsorbable polymers, the coating, if used, could be either biostable or bioabsorbable. However, as stated above, no coating may be necessary because the device itself is fabricated from a delivery depot. This embodiment offers a number of advantages. For example, higher concentrations of the therapeutic agent or agents may be achievable such as about >50% by weight. In addition, with higher concentrations of therapeutic agent or agents, regional drug delivery (>5 mm) is achievable for greater durations of time. This can treat different lesions such as diffused lesions, bifurcated lesions, small and tortuous vessels, and vulnerable plaque. Since these drug loaded stents or other devices have very low deployment pressures (3 to 12 atmospheres), it will not injure the diseased vessels. These drug-loaded stents can be delivered by different delivery systems such balloon expandable; self-expandable or balloon assist self-expanding systems.

In yet another alternate embodiment, the intentional incorporation of ceramics and/or glasses into the base material may be utilized in order to modify its physical properties. Typically, the intentional incorporation of ceramics and/or glasses would be into polymeric materials for use in medical applications. Examples of biostable and/or bioabsorbable ceramics or/or glasses include hydroxyapatite, tricalcium phosphate, magnesia, alumina, zirconia, yittrium tetragonal polycrystalline zirconia, amorphous silicon, amorphous calcium and amorphous phosphorous oxides. Although numerous technologies may be used, biostable glasses may be formed using industrially relevant sol-gel methods. Sol-gel technology is a solution process for fabricating ceramic and glass hybrids. Typically, the sol-gel process involves the transition of a system from a mostly colloidal liquid (sol) into a gel.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope for the appended claims.

What is claimed is:

1. An implantable medical device comprising:
a polymeric frame structure having at least two hoop components arranged in spaced apart relationship along a longitudinal axis, wherein adjacent hoop components are interconnected by at least one flexible connector, each of the hoop components being formed as a continuous series of substantially longitudinally oriented radial strut members and alternating substantially circumferentially oriented radial arc members connected in a repeating arrangement to form a substantially sinusoidal pattern, the at least one flexible connector being connected between longitudinally adjacent radial arc members, each end of each of the radial strut members having a reduced cross section hinge region configured such that when the frame structure is expanded, strain is concentrated in each hinge region, wherein each hinge region is formed at opposing ends of one of the radial strut members by a transition region that exhibits a tapering cross section from an increased cross section middle region formed longitudinally by opposing convex surfaces, wherein each radial arc member has a cross section greater than the increased cross section middle region and wherein the increased cross section middle region has a cross section greater than a remainder of the radial strut.

2. The implantable medical device of claim 1, wherein each hinge region has a smaller cross-sectional area relative to the adjacent geometry.

3. The implantable medical device of claim 1, wherein strain is concentrated in each hinge region when the polymeric frame structure is expanded.

4. The implantable medical device of claim 3, wherein the concentrated strain in each hinge region exceeds the yield point of the polymeric frame structure.

5. The implantable medical device of claim 4, wherein the concentrated strain in each hinge region is below the ultimate strain levels of the polymeric frame structure.

6. The implantable medical device of claim 3, wherein the concentrated strain in each hinge region is between 5 and 150 percent.

7. The implantable medical device of claim 3, wherein the concentrated strain in each hinge region is between 30 and 80 percent.

8. The implantable medical device of claim 1, wherein at least one of the radial arc members has constant radial thickness and a greater width than each hinge region.

9. The implantable medical device of claim 1, wherein the polymeric frame structure includes one or more sections being formed from at least one polymer and at least one plasticizer blended to create a deformable frame structure having increased toughness.

10. The implantable medical device of claim 9, wherein the at least one polymer is a bioabsorbable polymer.

11. The implantable medical device of claim 10, wherein the bioabsorbable polymer comprises a poly (α-hydroxy ester).

12. The implantable medical device of claim 10, wherein the bioabsorbable polymer comprises a poly (α-hydroxy ester) selected from the group consisting of poly (lactic acid), poly (glycolic acid), poly (caprolactone), poly (ρ-dioxanone), poly (trimethylene carbonate), poly (oxaesters), poly (oxaamides), and their co-polymers and blends.

13. The implantable medical device of claim 10, wherein the bioabsorbable polymer comprises a tyrosine derived poly (amino acid).

14. The implantable medical device of claim 13, wherein the tyrosine derived poly (amino acid) comprises poly (DTH carbonates).

15. The implantable medical device of claim 13, wherein the tyrosine derived poly (amino acid) comprises poly (arylates).

16. The implantable medical device of claim 13, wherein the tyrosine derived poly (amino acid) comprises poly (imino-carbonates).

17. The implantable medical device of claim 10, wherein the bioabsorbable polymer comprises a phosphorous containing polymer.

18. The implantable medical device of claim 17, wherein the phosphorous containing polymer comprises poly (phosphoesters).

19. The implantable medical device of claim 17, wherein the phosphorous containing polymer comprises poly (phosphazenes).

20. The implantable medical device of claim 10, wherein the bioabsorbable polymer comprises a polyalkanoate.

21. The implantable medical device of claim 20, wherein the polyalkanoate comprises a poly (hydroxybutyrate) (HB).

22. The implantable medical device of claim 20, wherein the polyalkanoate comprises a poly (hydroxybutyrate) (HB) and poly (hydroxyvalerate) (HV) and copolymers.

23. The implantable medical device of claim 9, wherein the at least one polymer comprises a biostable polymer.

24. The implantable medical device of claim 9, wherein the at least one polymer comprises a biostable polymer selected from the group consisting of polyurethanes, fluorinated materials, polyesters, polyamides, polyolefins, and their blends.

25. The implantable medical device of claim 1, wherein the polymeric frame structure comprises a therapeutic agent.

26. The implantable medical device of claim 25, wherein the therapeutic agent is dispersed uniformly in the polymeric frame structure.

27. The implantable medical device of claim 25, wherein the therapeutic agent comprises sirolimus.

28. The implantable medical device of claim 25, wherein the therapeutic agent comprises analogs of sirolimus.

29. The implantable medical device of claim 1, wherein the polymeric frame structure comprises a radiopaque agent.

30. The implantable medical device of claim 29, wherein the radiopaque agent is dispersed uniformly in the polymeric frame structure.

31. The implantable medical device of claim 1, wherein the polymeric frame structure comprises one or more sections being formed from a blended polymer to make the polymeric frame structure deformable having increased toughness.

32. The implantable medical device of claim 1, wherein the polymeric frame structure comprises a plasticizer.

33. The implantable medical device of claim 32, wherein the plasticizer comprises an organic plasticizer.

34. The implantable medical device of claim 33, wherein the organic plasticizer comprises a citrate ester.

35. The implantable medical device of claim 33, wherein the organic plasticizer comprises a polyethylene glycol.

36. The implantable medical device of claim 33, wherein the organic plasticizer comprises a solvent.

37. The implantable medical device of claim 1, wherein the polymeric frame structure comprises at least one polymer having a molecular orientation wherein the molecular orientation is selected from the group consisting of uniaxial, biaxial, or multiaxial.

38. The implantable medical device of claim 37, wherein the molecular orientation is biaxial.

39. The implantable medical device of claim 38, wherein the biaxial orientation comprises a longitudinal direction and a circumferential direction.

* * * * *